(12) United States Patent
Gutierro Aduriz et al.

(10) Patent No.: US 10,085,936 B2
(45) Date of Patent: *Oct. 2, 2018

(54) ANTIPSYCHOTIC INJECTABLE DEPOT COMPOSITION

(71) Applicant: LABORATORIOS FARMACEUTICOS ROVI, S.A., Madrid (ES)

(72) Inventors: Ibon Gutierro Aduriz, Madrid (ES); Maria Teresa Gomez Ochoa, Madrid (ES)

(73) Assignee: LABORATORIOS FARMACEUTICOS ROVI, S.A., Madrid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/690,647

(22) Filed: Nov. 30, 2012

(65) Prior Publication Data

US 2013/0171202 A1 Jul. 4, 2013

Related U.S. Application Data

(63) Continuation-in-part of application No. PCT/EP2011/059000, filed on May 31, 2011.

(30) Foreign Application Priority Data

May 31, 2010 (EP) ..................................... 10382154

(51) Int. Cl.
| | | |
|---|---|---|
| A61K 9/00 | (2006.01) | |
| A61K 31/519 | (2006.01) | |
| A61K 47/34 | (2017.01) | |

(52) U.S. Cl.
CPC .......... *A61K 9/0002* (2013.01); *A61K 9/0024* (2013.01); *A61K 31/519* (2013.01); *A61K 47/34* (2013.01)

(58) Field of Classification Search
CPC .. A61K 9/0002; A61K 31/519; A61K 9/0024; A61K 47/34
USPC .......................... 424/400; 514/259.41, 772.3
See application file for complete search history.

(56) References Cited

U.S. PATENT DOCUMENTS

| | | |
|---|---|---|
| 3,636,956 A | 1/1972 | Schneider |
| 3,773,919 A | 11/1973 | Boswell |
| 4,389,330 A | 6/1983 | Tice |
| 4,523,591 A | 6/1985 | Kaplan |
| 4,530,840 A | 7/1985 | Tice |
| 4,938,763 A | 7/1990 | Dunn |
| 5,620,700 A | 4/1997 | Berggren |
| 5,688,801 A | 11/1997 | Mesens |
| 5,770,231 A | 6/1998 | Mesens |
| 6,143,314 A | 11/2000 | Chandrashekar |
| 6,331,311 B1 | 12/2001 | Brodbeck |
| 6,565,874 B1 | 5/2003 | Dunn |
| 6,630,155 B1 | 10/2003 | Chandrashekar |
| 6,673,767 B1 | 1/2004 | Brodbeck |
| 6,773,714 B2 | 8/2004 | Dunn |
| 6,803,055 B2 | 10/2004 | Mesens |
| 7,118,763 B2 | 10/2006 | Mesens |
| 8,076,448 B2 | 12/2011 | Moore |
| 8,221,778 B2 | 7/2012 | Siegel |
| 8,324,343 B2 | 12/2012 | Moore |
| 2002/0023409 A1* | 2/2002 | Py .................................. 53/426 |
| 2004/0010224 A1* | 1/2004 | Bodmeier ...................... 604/82 |
| 2004/0247870 A1 | 12/2004 | Brown |
| 2005/0003007 A1 | 1/2005 | Boix |
| 2005/0042294 A1 | 2/2005 | Thanoo |
| 2007/0003596 A1* | 1/2007 | Tittelbach et al. ........... 424/426 |
| 2007/0077304 A1 | 4/2007 | Luk |
| 2008/0287464 A1 | 11/2008 | Wright |
| 2009/0305957 A1 | 12/2009 | Moore |
| 2010/0021544 A1* | 1/2010 | Bourges et al. .............. 424/486 |
| 2010/0266655 A1 | 10/2010 | Dadey |
| 2010/0292195 A1 | 11/2010 | Dadey |
| 2012/0108511 A1 | 5/2012 | Moore |

(Continued)

FOREIGN PATENT DOCUMENTS

| | | | |
|---|---|---|---|
| WO | WO 2007/041410 | * | 4/2007 |
| WO | WO 2008/059058 | * | 5/2008 |

(Continued)

OTHER PUBLICATIONS

Yapar et al. ("Effects of solvent combinations on drug release from injectable phase sensitive liquid implants", in Turk. J. Pharm. Sci. (2010), 7(1), 49-56).
Prashanth et a. ("Formulation and characterization of in situ implant of octeotride acetate", in Int. J. Pharm. (2013), 3(3), 565-573).
Calis et al. ("Influence of irradiation sterilization on poly(lactide-co-glycolide) microspheres containing anti-inflammatory drugs", in Il Farmaco (2002), 57, 55-62).
Wang et al. ("Design of a long-term antipsychotic in situ forming implant and its release control method and mechanism", Int. J. Pharm., May 10, 2012;427(2):284-92.
Maryott et al. (Table of Dielectric Constants of Pure Liquids, National Bureau of Standards, Circular No. 514, Aug. 10, 1951).
Gouw et al. (Physical Properties of Triglycerides IV. Dielectric Constant, Fette Seifen Anstrichmittel, (1967), 69(4), 223-226).

(Continued)

*Primary Examiner* — Katherine Peebles
(74) *Attorney, Agent, or Firm* — Innovar, L.L.C.; Rick Matos

(57) ABSTRACT

The present invention is directed to a composition that can be used to deliver an antipsychotic drug such as risperidone as an injectable in-situ forming biodegradable implant for extended release providing therapeutic plasma levels from the first day. The composition is in the form of drug suspension on a biodegradable and biocompatible copolymer or copolymers solution using water miscible solvents that is administered in liquid form. Once the composition contacts the body fluids, the polymer matrix hardens retaining the drug, forming a solid or semisolid implant that releases the drug in a continuous manner. Therapeutic plasma levels of the drug can be achieved since the first day up to at least 14 days or more even up to at least four weeks.

20 Claims, 18 Drawing Sheets

(56) References Cited

U.S. PATENT DOCUMENTS

| | | |
|---|---|---|
| 2013/0177603 A1 | 7/2013 | Gutierro Aduriz et al. |
| 2015/0147398 A1 | 5/2015 | Gutierro Aduriz et al. |
| 2015/0150791 A1 | 6/2015 | Gutierro Aduriz et al. |
| 2015/0196485 A1 | 7/2015 | Franco Rodriguez et al. |

FOREIGN PATENT DOCUMENTS

| | | | |
|---|---|---|---|
| WO | WO 2008/153611 | * | 12/2008 |
| WO | 2011/151356 A3 | | 12/2011 |
| WO | 2013/178811 A1 | | 12/2013 |
| WO | 2013/178812 A1 | | 12/2013 |

OTHER PUBLICATIONS

Lide (Properties of Common Laboratory Solvents, CRC Handbook of Chemistry and Physics 84th Ed., 2003-2004, Sect. 15-14, CRC Press, New York).

* cited by examiner

ANTIPSYCHOTIC INJECTABLE DEPOT COMPOSITION

CROSS-REFERENCE TO EARLIER FILED APPLICATIONS

The present application claims the benefit of PCT/EP2011/059000, filed May 31, 2011, which claims the benefit of EP 10382154.2 filed May 31, 2010, the entire disclosures of which are hereby incorporated by reference.

FIELD OF THE INVENTION

The present invention relates to implantable compositions that form extended drug-delivery devices comprising certain atypical antipsychotic drugs, particularly risperidone. Specifically, the present invention is related to compositions for injectable in-situ forming biodegradable implants comprising risperidone.

BACKGROUND OF THE INVENTION

Risperidone is an atypical antipsychotic drug with benzisoxazole and piperidine functional groups. It acts as a strong dopaminergic antagonist and selective serotonin receptor antagonist. Risperidone is FDA approved for the treatment of schizophrenia since 1993. It is the only drug presently approved for the treatment of schizophrenia in young people under 18 years, and together with lithium, for the treatment of bipolar disorders in children/youth ages between 10-18 years old. Conventional risperidone therapy of schizophrenia involves daily oral tablets, although it is also available as a solution and orally disintegrating tablets.

In fact, one of the intrinsic problems that risperidone-targeted patients usually face is the dissociation (non-compliance) of some schizophrenic patients from the treatment, especially when it therapy consists of a daily dosing, leading to irregular or inconstant treatments and thereby promoting the occurrence of psychotic episodes and crisis. Moreover, this kind of therapy gives rise to high fluctuations in plasma levels (measured as the difference between Cmax and Cmin) in patients, thereby usually affecting the patient's mood.

Risperidone is, therefore, a good drug candidate for incorporation into sustained delivery devices, where the patients would be covered or treated for long time periods with just one dose and without the need of caregivers to pay attention to a daily administration, and where a more homogeneous or level plasma concentration in the patient is desirable.

One of the most usual ways to administer risperidone presently is through the use of depot injections. Depot injections allow careful control of drug usage (as opposed to orally administered drugs) and ensure regular contact between the caregivers team and the patient, where overall treatment efficacy and/or side effects may be identified. Furthermore, it is easy to identify non-compliant patients and prepare interventions. However, in situ forming implants currently described in the state of the art cannot properly control risperidone release from the implant, and fail to allow obtaining therapeutic plasma levels in a bi-weekly administration protocol, with reasonable differences between maximum and minimum concentrations.

Currently, the long-acting injectable risperidone formulation, Risperdal Consta®, is the first depot dosage form with an atypical antipsychotic drug in the market. It is an intramuscular risperidone-containing PLGA microparticle formulation, and it is intended to deliver therapeutic levels of risperidone suitable for bi-weekly administration. However, due to the inherent lag phase of most microparticle based products, the patient is required to supplement the first weeks with daily doses of oral risperidone after first administration. Approximately three weeks after a single intramuscular injection of Risperdal Consta® and concurrent daily doses of oral risperidone, the microspheres release sufficient risperidone in the systemic circulation that the patient can discontinue supplementation with daily doses of the oral therapy. However, this period of oral supplementation presents a risk factor for non-compliance. Also, the presence in the body of two doses at the same time could present a potential risk of adverse events, such as irregular formulation behavior and toxicity (occurrence of unwanted side effects).

The compositions of the invention are based on a biodegradable copolymer poly(L-lactide-co-glycolide) matrix. These polymers have been used for many years in medical applications like sutures described in U.S. Pat. No. 3,636,956 by Schneider, surgical clips and staples described in U.S. Pat. No. 4,523,591 by Kaplan et al., and drug delivery systems described in U.S. Pat. No. 3,773,919 by Boswell et al. However, most of the existing formulations using these biodegradable polymers require manufacturing of an implantable device in solid form prior to the administration into the body, which device is then inserted through an incision or is suspended in a vehicle and then injected. In such instances, the drug is incorporated into the polymer and the mixture is shaped into a certain form such as a cylinder, disc, or fibre for implantation. With such solid implants, the drug delivery system has to be inserted into the body through an incision. These incisions are sometimes larger than desired by the medical profession and occasionally lead to a reluctance of the patients to accepts such an implant or drug delivery system.

U.S. Pat. No. 8,221,778 to Siegel et al. (corresponding to WO 2005/070332) discloses an implant containing risperidone (10-60% wt) and PLGA (90-40% wt) having a lactic acid to glycolic acid ratio of 50:50 to 100:0. These implants are not formed in situ.

Injectable biodegradable polymeric matrix implants based on lactic acid, glycolic acid and/or their copolymers for sustained release have been described in the art. U.S. Pat. No. 5,620,700 issued to Berggren describes a bioerodible oligomer or polymer material containing drug for local application into a diseased tissue pocket such as a periodontal pocket. However, the material requires heating to high temperatures to become sufficiently flowable to allow the injection, so that hardening of the material after cooling to the body temperature forms the implant.

U.S. Pat. No. 6,143,314 to Chandrashekar discloses an injectable composition that forms an implant in situ. The composition is made of drug, organic solvent and a PLGA/PEG block copolymer.

U.S. Pat. No. 6,673,767 issued to Brodbeck describes procedures for in situ formation of biodegradable implants by using biocompatible polymers and biocompatible low water-miscible solvents. A viscous polymeric solution containing the drug that upon injection releases the drug in a controlled manner is obtained through the use of low water-soluble solvents. Solvents with low water-solubility (less than 7% miscibility in water) are used as a way to reduce the release of the drug in aqueous mediums, allowing initial drug releases of 10% or lower during the first 24 hours. However, in our experience, the use of water-immiscible and/or low water-miscible solvents cannot satisfactorily control the initial in vivo release of risperidone during the first 24 hours. For example, the use of benzyl alcohol, a solvent specifically included in U.S. Pat. No. 6,673,767, causes very high plasma levels of risperidone in the first 3 days and then the plasma levels decrease to very low levels in 7 days.

U.S. Pat. No. 6,331,311 issued to Brodbeck also discloses injectable depot compositions comprising a biocompatible polymer such as PLGA, a solvent such as N-methyl-2-pyrrolidone and a beneficial agent such as a drug, further comprising an emulsifying agent such as polyols. However, the compositions disclosed do not perform satisfactorily when the beneficial agent is risperidone, because the use of a two-phase composition with emulsifying agents accelerates implant hydration and increases effective releasing surface area, impairing the control on the initial burst release and causing a fast decrease in drug release from the first days to the following ones. For example, a comparator composition was prepared according to the '311 patent. A container containing risperidone (150 mg), PLGA (300 mg, having an inherent viscosity of 0.32 dl/g and irradiated by β-irradiation to a dose of 25 KGy) and NMP (700 mg) was prepared. Another container containing polyvinyl alcohol in water (1 ml of a 2% w/v). The contents of the containers were mixed, then the mixture was transferred to a syringe and injected intramuscularly (an amount equivalent to 2.5 mg risperidone) into the gluteus of New Zealand White rabbits (n=3). More than 70% of the total AUC of active moiety was released within the first 5 days after the injection. Such a formulation is unable to provide therapeutic plasma levels of risperidone for a period of at least two weeks.

U.S. Pat. No. 4,938,763, issued to Dunn et al., discloses a method for an injectable in situ forming implant. A biodegradable polymer or copolymer dissolved in a water-miscible solvent with a biologically active agent either is dissolved or dispersed within the polymeric solution. Once the polymeric solution is exposed to body fluids, the solvent diffuses and polymer solidifies entrapping the drug within the polymer matrix. Even though Dunn et al. discloses the use of water miscible solvents for obtaining in situ forming polymeric implants, it discloses a number of polymers and solvents and even proportions between the different ingredients that do not produce a satisfactory implant with the appropriate release characteristics, particularly when the implant contains risperidone as active principle. For example, a comparator composition was prepared according to the '763 patent. A container containing risperidone (50 mg) and PLGA (784 mg, monomer ratio of lactic acid to glycolic acid monomer of 75:25, and having an inherent viscosity of 0.20 dl/g was prepared. Another container containing NMP (1666 mg) was prepared. The contents of the containers were mixed. Then the mixture was transferred to a syringe and a portion (1250 mg, corresponding to 25 mg of risperidone) was injected into an aqueous liquid to determine its in vitro release profile. More than 50% of the risperidone was released within the first 2 days. Such a formulation is unable to provide therapeutic plasma levels of risperidone for a period of at least two weeks.

Another way to avoid surgery for administering these drugs is injection of small-sized polymeric particles, microspheres or microparticles containing the respective drug. U.S. Pat. No. 4,389,330 and U.S. Pat. No. 4,530,840 describe a method for the preparation of biodegradable microparticles. U.S. Pat. No. 5,688,801 and U.S. Pat. No. 6,803,055 disclose microencapsulation of 1,2-benzazoles into polymeric particles to achieve a drug release over extended periods of time in the treatment of mental disorders. These microparticles require resuspension into aqueous solvents prior to the injection. These formulations do not form a single (nonparticulate) solid implant.

U.S. Pat. No. 5,770,231 describes a method for producing biodegradable microparticles for sustained release of risperidone and 9-hydroxy-risperidone by dissolving the drug within an organic phase. However, the use of organic solvents that are able to dissolve the risperidone mostly or completely gives rise to very high initial plasma levels of risperidone, after implantation of the particles, due to the diffusion of the drug along with the diffusion of the solvent.

U.S. Pat. No. 7,118,763 describes two methods of making multi-phase sustained-release microparticle formulations based on the combination of different particle sizes or microparticles exhibiting different release profiles. The combination of two different release profiles allows the release of the drug for periods longer than two weeks. However, in practice this combination requires a mixture of particles from at least two different batches, involving the multiplication of end product specifications and increasing batch-to-batch variability.

WO 2008/153611 A2 discloses numerous sustained delivery systems of risperidone and a metabolite. Risperidone is mixed with a soluble thermoplastic polymer, forming an encapsulating residue upon injection from which risperidone is slowly released. However, the authors failed to recognize the influence of process parameters and of specific result effective variables on the initial risperidone burst. In particular, none of the formulations contained a risperidone/polymer mass ratio between 25 and 35%, as in the presently claimed formulations. Moreover, all the tests disclosed therein were carried out using a specific solvent, namely N-methyl-2-pyrrolidone (NMP).

Although microparticle formulations can be administered by injection, they cannot always satisfy the demand for a biodegradable implant because they sometimes present difficulties in the large-scale production. Moreover, in case of any medical complication after injection, they are more problematic to be removed from the body than implantable compositions such as those of the invention.

Therefore, the compositions already described in the state of the art fail to provide suitable extended release risperidone compositions, kits and treatments for psychiatric disorders, and there still exists a need of compositions and devices to allow a controlled, constant release of the drug during prolonged periods of time.

SUMMARY OF THE INVENTION

The present invention seeks to overcome one or more of the disadvantages of known depot formulations containing an atypical anti-psychotic. Contrary to known injectable depot compositions, the compositions of the invention provide an easier method for the production of a single unit implantable device allowing constant and effective plasma levels during a period comprising from the first day up to at least 14 days or at least up to 4 weeks. The compositions of the invention are injected as a liquid or semisolid formulation that precipitates by solvent diffusion after injection into a subject and forms a single (not multiparticulate) solid implant at an injection site.

The risperidone-containing compositions of the invention provide therapeutic drug plasma levels from the first day up to at least 14 days after implantation, thereby avoiding the need of supplementary oral daily therapy from the administration moment. These compositions can also reduce the fluctuations between Cmax and Cmin, especially as compared to those observed with daily administration of oral tablets, and subsequently may reduce variations in the patient mood caused by excessive plasma level fluctuations. In addition, they can also cover a dosing period that is at least as long as the dosing periods covered by currently marketed extended-release risperidone-containing formulations.

Some of the key points where the compositions of the invention show improvements over the state of the art include:
Stability, by using a solid product for reconstitution previous to injection;
Pharmacokinetic Profile:
    Onset: The compositions of the invention show plasma therapeutic levels from the first day after administration, avoiding the 2-3 weeks lag time that the currently marketed long-term risperidone product shows.
    Duration: The compositions of the invention may allow an increase in the interval between administrations as compared to currently marketed long-term risperidone product.
Plasma levels: The compositions of the invention induce more sustained plasma levels, and with lower differences between Cmax and Cmin than the currently marketed long-term risperidone product.

The present inventors have identified that the initial burst release of the drug can be satisfactorily controlled during at least 2 weeks by controlling at least one of the following factors, either alone or in combination:
the viscosity of the polymeric solution;
the risperidone/polymer mass ratio in the implant;
the risperidone particle size;
the polymeric solution/drug mass ratio; and
the solvent/risperidone mass ratio.

It should be noted that there was little recognition if any in the art that the above-enumerated variables would be result effective in terms of their impact upon the initial release of risperidone after implantation or after placement in an aqueous fluid. By adequately controlling at least some of these result effective variables, release of drug from the implant during at least the first two weeks can be precisely controlled, allowing satisfactory release profiles from the very first day until at least 14 days, and achieving in some cases more than 30 days and up to 40 days following administration of a single dose within a dosing period.

The invention provides injectable compositions and corresponding kits in which a solid polymer or copolymer is dissolved in a solvent, which is non-toxic and water miscible, to form a liquid polymeric solution, which is mixed with risperidone. When these compositions are exposed to body fluids or water, the solvent diffuses away from the polymer-drug mixture and water diffuses into the mixture where it coagulates the polymer thereby trapping or encapsulating the drug within the polymeric matrix as the implant solidifies into a single body. The release of the drug then follows the general characteristics for diffusion or dissolution of a drug from within a polymeric matrix. Drug is also released by polymer erosion/degradation. The risperidone forms a suspension or dispersion within a biodegradable and biocompatible polymeric solution to form an injectable composition that can be administered by means of a syringe and a needle. The composition solidifies inside the body by solvent diffusion, thereby forming the single implant at the site of injection.

One aspect of the invention provides an injectable composition as described and/or exemplified herein. The compositions of the invention comprise at least a polymer matrix, a solvent for the polymer and a drug, wherein the composition is defined by certain selected ranges and ratios of at least one of the following parameters, either alone or in combination:
the viscosity of the polymeric solution (polymer+solvent) or injectable composition;
the risperidone/polymer mass ratio; and/or
the risperidone particle size.

Additional parameters such as the mass ratio between the amounts of polymeric solution (polymer+solvent) and drug, and the solvent/drug mass ratio, can also be useful to provide control over the initial release of risperidone from the compositions of the invention.

A first aspect of the invention provides an injectable depot composition, comprising:
    a. a drug, such as is risperidone and/or its metabolites or prodrugs in any combination thereof;
    b. at least a biocompatible polymer which is a copolymer comprising lactic acid and glycolic acid monomers, wherein the monomers are present at a monomer ratio of lactic to glycolic acid in the range from about 48:52 to about 77:23, and
    c. at least a water-miscible solvent with a dipole moment about 3.9-4.3 D,
wherein the solvent and polymer form a polymer solution having a viscosity in the range of 0.5 to 3.0 Pa·s, and the solvent/drug mass ratio ranges from about 10:1 to about 4:1, characterised in that the drug/polymer mass ratio is between 25 and 35% expressed as the weight percentage of the drug with respect of the drug plus polymer.

Embodiments of the invention include those wherein the drug is present in freebase form, in salt form or a mixture thereof.

In some embodiments, the concentration of the polymeric component in the injectable composition is in the range of about 25-50%, (expressed as the percentage of polymer weight based on total polymeric solution component) and or about 30-40%.

In some embodiments, the injectable composition has a viscosity in the range of about 0.5-7.0 Pa·s, more preferably about 0.5-3.0 Pa·s, and most preferably about 0.7-3.0 Pa·s.

In some embodiments, the concentration of drug in the injectable composition is generally in the range of about 4 to about 16% wt, expressed as the percentage of the drug with respect to the total composition weight.

In some embodiments, the compositions of the invention comprise a biodegradable poly(L-lactide-co-glycolide) copolymer (PLGA) matrix. The monomer ratio of lactic acid to glycolic acid monomers present in the polymer can range from about 45:65 to about 75:25, about 50:50 to about 75:25, about 50:50 to about 70:30, about 50:50 to about 65:35, or about 65:35 to about 75:25. In some embodiments, the intrinsic or inherent viscosity of the polymer is in the range of about 0.16 to about 0.60 dl/g when measured in chloroform at 25° C. and a 0.1% (wt/v) concentration. In some embodiments, the PLGA copolymer is end-capped. In some embodiments, the PLGA copolymer is irradiated with beta-radiation prior to inclusion in the injectable composition. In some embodiments, a commercially available PLGA copolymer has an initial intrinsic viscosity that is to high for use but after irradiation with beta-radiation it has an intrinsic viscosity that is within the ranges specified herein thereby rendering it suitable for use in the injectable composition.

The use of a solvent having a dipole moment in the range of about 3.9-4.3 D results in an implant that provides suitable initial plasma levels of risperidone and therefore a better control of the release of the drug during the first 5 days after the injection. This solvent effect on the release of risperidone is completely unexpected. Embodiments of the invention include those wherein the solvent is selected from the group consisting of DMSO, NMP, PEG or a combination thereof.

The invention also provides an injectable composition that forms a single solid body implant in a subject to which it is administered, the composition comprising:

a. a polymeric solution comprising a biodegradable poly (L-lactide-co-glycolide) polymer having a monomer ratio of lactic acid to glycolic acid in the range of 50:50 to 75:25, and a solvent having a dipole moment in the range of 3.9-4.3 D, wherein the solvent is present in an amount sufficient to dissolve the polymer; and b. drug-containing particles of risperidone, a metabolite of risperidone, a prodrug of risperidone or a combination thereof at least partially dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution is in the range of about 60-130 microns; wherein c. the intrinsic or inherent viscosity of the polymer is in the range of about 0.16 to about 0.60 dl/g when measured in chloroform at 25° C. and a 0.1% concentration;

d. the viscosity of the polymeric solution is in the range of about 0.5-7.0 Pa·s;

e. the concentration of drug in the injectable composition is in the range of about 4 and 16 wt %, expressed as the percentage of the drug with respect to the total composition weight, or the mass ratio of the amount of polymeric solution (polymer+solvent) to the amount of drug in the injectable composition ranges from about 15:1 to 5:1;

f. the concentration of polymer in the injectable composition is in the range of about 25-50% expressed as the percentage of polymer weight based on total polymeric solution component; and g. the composition has a solvent/drug mass ratio ranging from about 10:1 to about 4:1.

In some embodiments, the composition is injectable by hand through a 18 to 22 gauge needle, and preferably through a 20-21 gauge needle.

Another aspect of the invention provides a pharmaceutical kit suitable for preparation of an injectable composition that forms a biodegradable non-particulate solid implant in situ in a subject in need thereof, the kit comprising: a first container comprising risperidone and a biocompatible polymer, and a second container comprising a water-miscible solvent in which the biocompatible polymer is soluble, whereby mixing of the contents of the first container with the contents of the second container affects formation of an injectable polymer solution composition as described herein. In some embodiments, the containers are syringes and the mixing of the contents of the first and second containers may be performed by direct or indirect connection followed by moving forwards and backwards the plungers of the syringes.

Embodiments of the invention include those wherein: a) the risperidone is present in solid form in the container prior to mixing with the solvent; b) the risperidone is present in particulate form or as a lyophilisate in the container prior to mixing with the solvent; c) the particle size distribution of the risperidone is as follows: not more than 10% of the total volume of drug particles are less than 10 microns in size and not more than 10% of the total volume of drug particles are greater than 225 microns in size; d) the d0.5 of the particle size distribution is in the range of about 60-130 microns; e) the mass ratio of the amount of polymeric solution (polymer+solvent) and to the amount of risperidone in the injectable composition ranges from about 15:1 to 5:1; f) the mass ratio of the amount of solvent and the amount of risperidone (mg solvent/mg risperidone) in the injectable composition ranges from about 12:1 to 4:1; g) the kit further comprises an alkaline agent; h) the mole ratio of risperidone to alkaline agent ranges from 2/3 to 2/5; i) the solvent, polymeric solution, risperidone and/or injectable composition is sterilized prior to administration; and/or j) the kit further comprises an alkaline agent in either or both containers.

Another aspect of the invention provides a method for preparing an injectable composition as described herein. In some embodiments, the method comprises:

a. subjecting a biodegradable poly(L-lactide-co-glycolide) polymer, having a monomer ratio of lactic acid to glycolic acid in the range of 50:50 to 75:25 and having a first molecular weight in a solvent to form a polymeric solution having a first viscosity, to a sufficient amount of β-irradiation to degrade at least a portion of the polymer thereby reducing its molecular weight and reducing the intrinsic viscosity of the polymer; and b) mixing the polymer with a solvent to form a polymeric solution, wherein the properties of the polymeric solution are as described herein; and wherein drug is included with the polymer or solvent prior to mixing or wherein drug is added to the polymeric solution after formation thereof, thereby forming the injectable composition.

In some embodiments, the invention provides a process for preparing an injectable composition, comprising: a) dissolving a polymer having a molecular weight greater than about 15 KDa in a solvent having a dipole moment about 3.9-4.3 D to form a polymeric solution having a viscosity greater than about 0.5 Pa·s, wherein the concentration of the polymer in the solution is in the range of about 25-50%, expressed as the percentage of polymer weight based on total solution weight, wherein the polymer comprises lactic acid and glycolic acid monomers, wherein the monomers are present at a monomer ratio of lactic acid to glycolic acid in the range of about 50:50 to 75:25; and b) subjecting the polymer to at least 10 KGy of β-irradiation to degrade at least a portion of the polymer thereby reducing its molecular weight to a range of about 25-52 KDa and reducing the viscosity of a respective polymeric solution thereof to a range of about 0.5 to 3.0 Pa·s. In some embodiments, drug is included in the polymeric solution, and the weight percentage of drug with respect to the total weight of drug plus polymer is in the range of about 25 to 35%.

Another aspect of the invention provides the use of an injectable depot composition as described herein for the treatment of schizophrenia or bipolar disorders in the human body. The method comprises administering to a subject in need thereof an amount of injectable depot composition as described herein sufficient to provide a therapeutic dose of risperidone for a period of at least two weeks following administration thereof.

Embodiments of the invention include those wherein: a) the composition is administered every two weeks, every three weeks, every four weeks or every five weeks during a treatment period; b) the composition provides a therapeutic plasma level of risperidone or other form thereof from within 24 hours after administration to at least 14 days after administration; c) the plasma level of active moiety ranges from about 5 to about 150 ng/ml and preferably from about 10 to about 100 ng/ml in the steady state during a dosing period; d) the implant provides an active moiety (risperidone+9-OH risperidone) plasma level within the range of about 5 to about 80 ng/ml when about 116 to about 700 mg, respectively, of the composition comprising about 25 to about 150 mg, respectively, of risperidone are administered via injection; e) the injectable composition is exposed to an aqueous fluid thereby forming a solid body which is then administered to a subject in need thereof; f) the injectable composition is formed within one month, within three weeks, within two weeks, within one week, within three days, within one day, within less than one day, within 18 hours, within 12 hours, within 6 hours, within 1 hour, within 15 minutes or within 5 minutes prior to administration to a subject; g) the injectable composition is warmed or cooled prior to administration to a subject; h) the polymer, solvent, polymer solution and/or drug is sterilized prior to administration; i) sterilization comprises sterilization of the drug or polymer by exposure to beta-irradiation in the range 5-25 KGy; j) sterilization comprises sterilization of the polymer solution by filtration through a filtration medium having a nominal pore size of 22 microns or less; and/or k) the composition is administered intramuscularly, intraperitoneally, intrathecally, intravaginally, subcutaneously, intracranially or intracerebrally. In some embodiments, the preferred mode of administration is intramuscular.

The specification discloses one or more embodiments that incorporate features of this invention. The scope of the present invention is not limited solely to the disclosed embodiments. The invention includes all combinations and sub-combinations of the various aspects and embodiments disclosed herein. These and other aspects of this invention will be apparent upon reference to the following detailed description, examples, claims and attached figures.

BRIEF DESCRIPTION OF THE FIGURES

The accompanying drawings, which are incorporated herein and form a part of the specification, illustrate one or more embodiments of the present invention and, together with the description, further serve to explain the principles of the present invention and to enable a person skill in the pertinent art to make and use the invention. The following drawings are given by way of illustration only, and thus are not intended to limit the complete scope of the present invention.

DETAILED DESCRIPTION OF THE INVENTION

Figure 1:
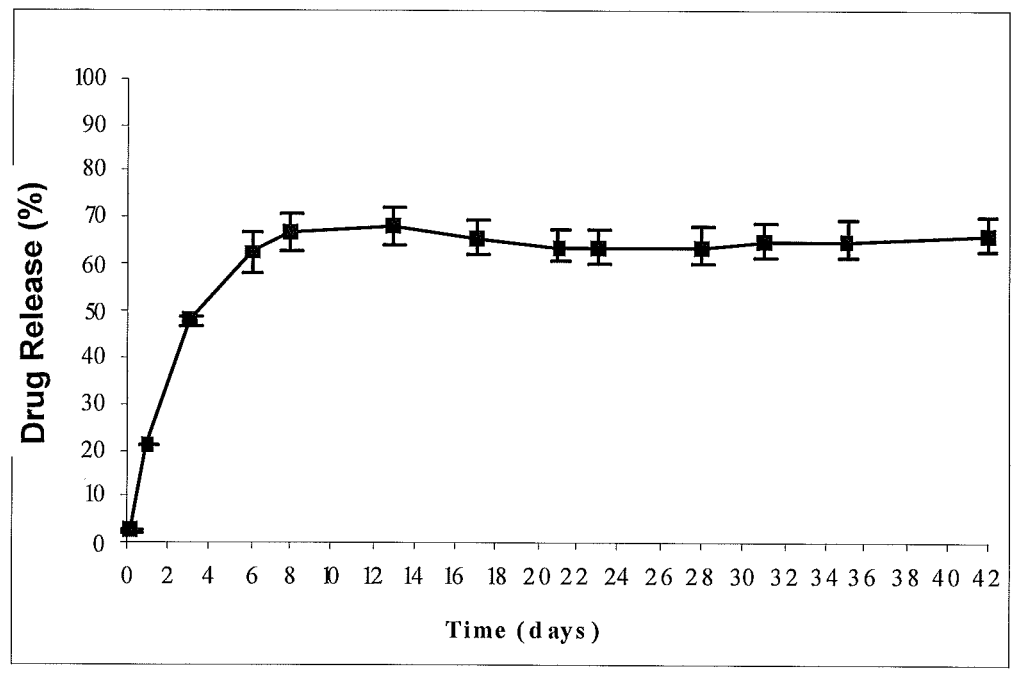
FIG. 1: In vitro release profile of risperidone for the composition of Comparative Example 1 (risperidone, polymer and a water-insoluble solvent).

As used herein and unless otherwise specified, the term "risperidone" refers to "4-[2-[4-(6-fluorobenzo[d]isoxazol-3-yl)-1-piperidyl]ethyl]-3-methyl-2,6-diazabicyclo[4.4.0]deca-1,3-dien-5-one" and to the salt, freebase, amorphous, crystalline, anhydrous, hydrate, optically pure, optically enriched or racemic forms thereof. Combinations of these various forms are also within the scope of the invention. The compositions of the invention can comprise risperidone, a metabolite thereof, e.g. paliperidone which is also known as "(RS)-3-[2-[4-(6-fluorobenzo[d]isoxazol-3-yl)-1-piperidyl]ethyl]-7-hydroxy-4-methyl-1,5-diazabicyclo[4.4.0]deca-3,5-dien-2-one", a prodrug thereof, a derivative thereof or a combination thereof.

Suitable pharmaceutically acceptable salts of risperidone, or a metabolite or derivative thereof, include the acid addition salts with hydrochloric acid, methane sulfonic acid, benzene sulfonic acid, tartaric acid, maleic acid, malic acid, ethane disulfonic acid, lactic acid, acetic acid, and mandelic acid. Exemplary salts include risperidone dihydrochloride, risperidone mesylate, risperidone hemitartrate, risperidone hydrogenmaleate, risperidone (L)-hemimalate, risperidone hemiedisylate, risperidone (L)-lactate, risperidone acetate monohydrate, and risperidone (R)-mandelate. Such salts can be prepared according to U.S. Publication No. 20040266791, the relevant disclosure of which is hereby incorporated by reference. Preferred salts of risperidone or paliperidone include those having a water solubility of less than or about 2 mg/ml. In some embodiments, risperidone, its metabolite and/or its derivative is present as a freebase in the injectable composition.

As used herein, the term "prodrug" is taken to mean a compound that is administered in an inactive (or less than fully active) form, and is subsequently converted to an active pharmacological agent through normal metabolic processes. A prodrug serves as a type of 'precursor' to the intended drug, e.g. risperidone. Exemplary prodrugs include the fatty acid esters of paliperidone (9-hydroxyrisperidone) as disclosed in U.S. Pat. No. 6,555,544, the entire disclosure of which is hereby incorporated by reference.

As used herein, the term "derivative" is taken to mean a compound that is obtained by chemical modification of a parent compound such that the "derivative" includes within it almost all or all of the chemical structure of the parent (or base) compound. A derivative is a compound that is formed from a similar compound or a compound that can be imagined to arise from another compound, if one atom is replaced with another atom or group of atoms. A derivative is a compound derived or obtained from another and containing essential elements of the parent substance. A derivative is a chemical compound that may be produced from another compound of similar structure in one or more steps.

As used herein, the term "polymeric solution" is taken to mean the fluid composition comprising a combination of the solvent and the polymer dissolved therein. In some embodiments, at least 80%, at least 90%, at least 95%, at least 99% or all of the polymer is dissolved in the solvent. If not otherwise specified, the viscosity value of the polymeric solution or the injectable composition is given in Pa·s units, measured in chloroform at 25° C. and at concentration of 0.1% wt/v.

By "satisfactorily controlled" release profile is meant that the implant will exhibit an initial release profile that is not too steep (fast), which would otherwise lead to plasma levels that are too high with concomitant toxic side effects, and an initial release profile that is not too flat (slow), which would lead to plasma levels that are below therapeutic concentrations. An implant exhibiting a satisfactorily controlled initial release profile will release 0.5 to 20% wt., 1 to 12% wt. or 2 to 8% wt of its charge of risperidone within 24 hours after being placed in an aqueous environment (liquid or subject). It will release no more than 20% wt., no more than 12% wt or no more than 8% wt of its charge of risperidone within 24 hours after being placed in an aqueous environment. It will release at least 0.5% wt., at least 2% wt. or at least 3% wt of its charge of risperidone within 24 hours after being placed in an aqueous environment.

The compositions of the invention comprise at least a polymer or polymer matrix, a solvent and a drug. The polymer is preferably a biocompatible and biodegradable polymer or polymer matrix. In order not to cause severe damage to the body following administration, the preferred polymers are biocompatible, non-toxic for the human body, not carcinogenic, and do not induce significant tissue inflammation. The polymers are preferably biodegradable in order to allow natural degradation by body processes, so that they are readily disposable and do not accumulate in the body. In selecting the appropriate grade of PLGA copolymer, the time required for degradation of PLGA is related to the monomer ratio used in production: the higher the content of glycolide units, the lower the time required for degradation. In addition, polymers that are end-capped with esters (as opposed to the free carboxylic acid) demonstrate longer degradation half-lives. The preferred polymers are selected from end-capped terminal carboxylic poly-lactide and polyglycolic acid copolymers (PLGA) mixed in a ratio from 50:50 to 75:25 (ratio of lactic acid monomer to glycolic acid monomer), with an intrinsic or inherent viscosity preferably in the range of 0.16-0.60 dl/g, and more preferably between 0.25-0.48 dl/g, as measured in chloroform at 25° C. and at a concentration of 0.1% wt/v with a Ubbelhode size 0 c glass capillary viscometer (RESOMER® grades) or as measured in chloroform at 30° C. and at a concentration of 0.5% wt/v with a size 25 Cannon-Fenske glass capillary viscometer (LAKESHORE MATERIALS™ grades). In some embodiments, the PLGA copolymer has a lactic acid to glycolic acid monomer ratio ranging from 48:52 to 52:48 or 48:52 to 77:23.

The concentration of the polymeric component in the compositions of the invention is preferably in the range of 25-50%, (expressed as the percentage of polymer weight based on total polymeric solution component) and more preferably between 30-40%. Suitable grades of PLGA copolymers as described herein (according to molecular weight, intrinsic viscosity and/or molar ratio of lactic acid monomer to glycolic acid monomer) are end-capped (such as with an ester group, e.g. lauryl ester, methyl ester) are available from EVONIK® (Essen, Germany), Boehringer Ingelheim (Ingelheim am Rhein, Germany), ALKERMES (Dublin, Ireland) or SIGMA ALDRICH(ST. Louis, Mo.) and are marketed under the tradenames RESOMER®, LAKESHORE BIOMATERIALS™, or MEDISORB®. As the composition of some grades of end-capped PLGA is proprietary, the identity of the ester end-cap is not publicly available. Nonetheless, the performance properties of the grades of PLGA copolymer described herein are known and are used to characterize the material. In some embodiments, the PLGA copolymer has an intrinsic viscosity, before irradiation, that is unsuitable for use in the injectable composition but, after irradiation, has an intrinsic viscosity that is suitable. Accordingly, a commercial material having an initially high intrinsic viscosity can still be used in the injectable composition provided it is irradiated so as to reduce its intrinsic viscosity to a value specified herein.

As used herein, the term intrinsic or inherent viscosity ($\eta_{inh}$) of the polymer is defined as the ratio of the natural logarithm of the relative viscosity, $\eta_r$, to the mass concentration of the polymer, c, i.e.:

$$\eta_{inh} = (\ln \eta_r)/c$$

and the relative viscosity ($\eta_r$) is the ratio of the viscosity of the solution $\eta$ to the viscosity of the solvent $\eta_s$, i.e.

$$\eta_r = \eta/\eta_s$$

If not otherwise specified, the intrinsic viscosity values throughout the present specification are to be understood as measured at 25° C. in chloroform at a concentration of 0.1%. The value of intrinsic viscosity is considered in the present specification, as commonly accepted in the art, as an indirect indicator of the polymer molecular weight. In this way, a reduction in the intrinsic viscosity of a polymer, measured at a given concentration in a certain solvent, with same monomer composition and terminal end groups, is an indication of a reduction in the polymer molecular weight (IUPAC. Basic definitions of terms relating to polymers; *Pure Appl. Chem.* (1974) 40, 477-491).

Suitable solvents are non-toxic, biocompatible and appropriate for parenteral injection. Solvents susceptible of causing toxicity should not be used for the injection of any material into any living body. Preferably, solvents are biocompatible in order not to cause severe tissue irritation or necrosis at the injection site. Therefore, the solvent is preferably classified as class II or III, and more preferably class III, according to ICH Guidelines. For the formation of the in-situ implant, the solvent should preferably diffuse quickly from the polymeric solution towards surrounding tissues when is exposed to physiological fluids. Consequently, the solvent is preferably water miscible and more preferably with a dipole moment about 3.9-4.3 D at 25° C. The preferred solvents are DMSO (dimethylsulfoxide), N-methyl-pyrrolidone (NMP) and PEG (poly(ethylene glycol, such as PEG having an average molecular weight in the range of about 200, about 300 or about 400). Grades of PEG that are liquid at ambient temperature (20-30° C.) may be used. The most preferred solvent is DMSO. The invention also includes an injectable composition having a combination of two or more of these solvents.

In some embodiments, the drug is completely dissolved, partially dissolved or completely undissolved in the solvent used to form the polymeric solution to form the injectable composition. The drug is preferably at least partly suspended, i.e. only partially dissolved, in the solvent or polymeric solution. In some embodiments, $\leq 5\%$, $\leq 10\%$, $\leq 20\%$, $\leq 30\%$, $\leq 40\%$, $\leq 50\%$, $\leq 60\%$, $\leq 70\%$, $\leq 80\%$, $\leq 90\%$, $\leq 95\%$, or $\leq 99\%$ wt of the drug is dissolved in the solvent or polymeric solution to form the injectable composition. In some embodiments, $\geq 1\%$, $\geq 5\%$, $\geq 10\%$, $\geq 20\%$, $\geq 30\%$, $\geq 40\%$, $\geq 50\%$, $\geq 60\%$, $\geq 70\%$ or up to about 80% wt. of the drug is dissolved in the solvent or polymeric solution to form the injectable composition.

The solubility of the drug in the solvent is preferably less than about 90 mg/ml, more preferably less than about 65 mg/ml, and most preferably below about 10 mg/ml. The advantage of this low solubility is that the initial burst of the drug when the solvent diffuses into the external aqueous medium, following placement therein, is greatly reduced.

In some embodiments, the concentration of drug in the injectable composition is generally in the range of about 4 and 16 wt %, expressed as the percentage of the drug with respect to the total composition weight. More preferably, the drug content is between 7 and 15% wt, and most preferably about 13% wt with respect to the total composition weight.

One of the factors contributing to controlling the initial release of drug from the implant, after placement in an aqueous environment, is the viscosity of the polymeric solution of the injectable composition. The term "polymeric solution" is defined as the combination of the polymer matrix and the solvent in which it is dissolved. In some embodiments, the polymeric solution has a viscosity in the range of about 0.5-7.0 Pa·s, more preferably about 0.5-3.0 Pa·s, and most preferably about 0.7-3.0 Pa·s.

Another factor contributing to controlling the initial release of drug from the implant is the risperidone/polymer mass ratio of the injectable composition. In some embodiments, this mass ratio, expressed as the percentage of the drug weight with respect to total weight of the drug plus polymer, is in the range of about 15-40% weight, more preferably about 25-35% wt, and most preferably about 33% wt.

Yet another factor contributing to controlling the initial release of drug from the implant is the drug's particle size. Large particles provide a smaller surface area per weight thereby reducing the initial release (burst) but the release may be then delayed until the beginning of the degradation of the polymeric matrix. On the other hand, small particles evoke higher burst levels due to increased surface area and easier drug diffusion from small particles during implant hardening, followed by continuous drug release levels due to the combination of the processes of drug diffusion and implant erosion. Consequently, in a preferred embodiment of the invention a wide particle size distribution, combining large and small particle sizes in different ratios, is used in order to reduce the initial burst and still maintain a suitable constant drug release by diffusion of smaller particles during the first phase of release and gradual release of drug from the bigger particles while the polymer degrades, i.e. during the period of time (days to weeks) following the initial burst phase. In some embodiments, the particle size distribution of the drug is as follows: not more than 10% of the total volume of drug particles are less than 10 microns in size (equivalent diameter in volume as a function of applying Fraunhofer theory to irregularly shape particles; as measured by laser light scattering, such as with a Malvem Mastersizer 2000) and not more than 10% of the total volume of drug particles are greater than 225 microns in size. In addition, the drug particles possess a d0.5 value preferably in the range of about 60-130 microns. Accordingly, in some embodiments, the risperidone comprises a broad particle size distribution, which can be monomodal, bimodal or trimodal.

In addition to the above factors, the following ratios between the components of the compositions according to the invention can also contribute toward controlling the initial release of drug from the implant: a) mass ratio between the amounts of polymeric solution (polymer+solvent) and risperidone in the injectable composition; b) mass ratio between the amounts of solvent and risperidone (mg solvent/mg risperidone) in the injectable composition; c) the presence or absence of an alkaline agent in the injectable composition.

In some embodiments, the mass ratio of the amount of polymeric solution (polymer+solvent) to the amount of risperidone in the injectable composition ranges from about 15:1 to 5:1, more preferably from about 12:1 to 5:1 and most preferably from about 7:1 to 6.5:1. In the most preferred embodiments, this mass ratio is about 6.66:1, or as described in the examples below (see Example 12).

In some embodiments, the mass ratio of the amount of solvent and the amount of risperidone (mg solvent/mg risperidone) in the injectable composition ranges from about 12:1 to 4:1, more preferably about 10:1 to 4:1 and most preferably about 5:1 to 4:1. In the most preferred embodiments, this mass ratio is about 4.66:1 (see Example 13 below). This ratio defines (is related to) the rate of hardening of the implant by solvent diffusion and consequently the precipitation of the polymer after the injectable composition is placed in a aqueous environment. Hence, this parameter is also related to the proportion of drug dissolved/dispersed in the polymeric solution and therefore it controls whether further drug is diffused from the implant or not.

Optionally, an alkaline agent with low water solubility such as lower than 0.02 mg/ml can be included within the polymer matrix. The alkaline agent can be present in a molar ratio >2/5 (drug/alkaline agent), meaning that the alkaline agent is present in molar excess over the drug. Preferred alkaline agents are alkaline or alkaline-earth hydroxides, such as magnesium hydroxide or aluminum hydroxide. Due to the limited water solubility of the alkaline agent, the d 0.5 of the particle size distribution, e.g. of the magnesium hydroxide, is preferably below 10 microns.

The invention also provides an injectable composition that forms a single solid body implant in a subject to which it is administered, the composition comprising:
  a. a polymeric solution comprising a biodegradable poly(L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns.

The invention also provides an injectable composition that forms a single solid body implant in a subject to which it is administered, the composition comprising:
  a. a polymeric solution comprising a biodegradable poly(L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein
  c. the intrinsic or inherent viscosity of the polymer is in the range of about 0.16 to about 0.60 dl/g when measured in chloroform at 25° C. and a 0.1% concentration.

The invention also provides an injectable composition that forms a single solid body implant in a subject to which it is administered, the composition comprising:
  a. a polymeric solution comprising a biodegradable poly(L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein
  c. the viscosity of the polymeric solution is in the range of about 0.5-7.0 Pa·s.

The invention also provides an injectable composition that forms a single solid body implant in a subject to which it is administered, the composition comprising:
  a. a polymeric solution comprising a biodegradable poly(L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein
  c. the concentration of drug-containing particles in the injectable composition is in the range of about 4 and 16 wt %, expressed as the percentage of the drug-containing particles with respect to the total composition weight, or the mass ratio of the amount of polymeric solution (polymer+solvent) and to the amount of drug-containing particles in the injectable composition ranges from about 15:1 to about 5:1.

The invention also provides an injectable composition that forms a single solid body implant in a subject to which it is administered, the composition comprising:
  a. a polymeric solution comprising a biodegradable poly (L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein
  c. the concentration of polymer in the injectable composition is in the range of about 25-50% expressed as the percentage of polymer weight based on total polymeric solution component.

The invention also provides an injectable composition that forms a single solid body implant in a subject to which it is administered, the composition comprising:
  a. a polymeric solution comprising a biodegradable poly (L-lactide-co-glycolide) polymer having a monomer ratio of lactic acid to glycolic acid in the range of 50:50 to 75:25, and a solvent having a dipole moment in the range of 3.9-4.3 D; and
  b. drug-containing particles of risperidone, a metabolite of risperidone, a prodrug of risperidone or a combination thereof dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution being in the range of about 60-130 microns; wherein
  c. the composition has a solvent/drug mass ratio ranging from about 10:1 to about 4:1.

Figure 35:
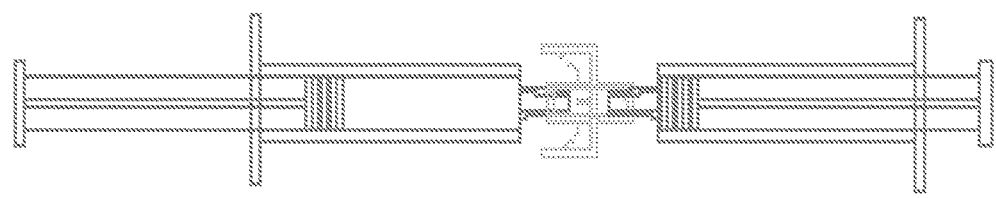
FIG. 35 depicts an exemplary kit comprising syringes connected through a connector device.
Figure 36:
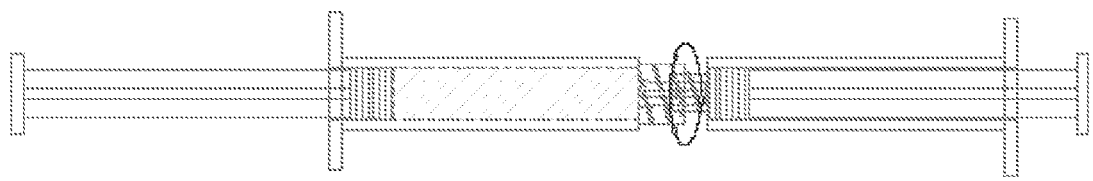
FIG. 36 depicts another exemplary kit comprising syringes connected through a direct thread.

Another aspect of the invention is directed to a kit comprising: a first container containing a polymer in solid form, risperidone and optionally $Mg(OH)_2$ in predetermined amounts; and a second container containing a water-miscible solvent. When required, the contents of both containers are combined, for example through a connector or by using male-female syringes, and mixed each other so that the compositions according to the invention are reconstituted, for example by moving forwards and backwards the plungers of the syringes. The polymer is preferably PLGA, which is preferably provided in freeze-dried (lyophilized) form. Each container is independently selected at each occurrence from a syringe, vial, device and cartridge. Each container is independently at each occurrence disposable or not disposable. Illustrative preferred embodiments of the containers are depicted in FIG. 35 (syringes connected through a connector device) and in FIG. 36 (syringes connected through a direct thread).

The invention also provides an injectable composition that forms a single solid body implant in a subject to which it is administered, the composition comprising:
  a. a polymeric solution comprising a biodegradable poly (L-lactide-co-glycolide) polymer having a monomer ratio of lactic acid to glycolic acid in the range of 50:50 to 75:25, and a solvent having a dipole moment in the range of 3.9-4.3 D, wherein the solvent is present in an amount sufficient to dissolve at least 95% of the polymer;
  b. drug-containing particles of risperidone, a metabolite of risperidone, a prodrug of risperidone or a combination thereof at least partially dispersed in the polymeric solution, the particles having a size distribution as follows: not more than 10% of the total volume of drug particles is less than 10 microns in size, not more than 10% of the total volume of drug particles is greater than 225 microns in size, and the d0.5 of the size distribution is in the range of about 60-130 microns; and
  c. $Mg(OH)_2$ present in molar excess over the moles of drug.

In a preferred embodiment, the injectable depot compositions of the invention further comprise $Mg(OH)_2$ at a molar ratio in the range of 2/3 to 2/5, expressed as the molar ratio of drug to $Mg(OH)_2$.

In some embodiments, the injectable depot composition is sterile as a finished product. The biocompatible polymer can be sterilized prior to its aseptic filling process, preferably by an aseptic filling process by beta-irradiation in the range 5-25 KGy or it can be sterilized after being dissolved in a solvent to form a polymeric solution followed by filtration of the polymeric solution through a filter with a 0.22 µm pore size or less.

The polymer can be sterilized by β-irradiation. Example 15 describes an exemplary process for sterilization of the composition. The polymer and risperidone were mixed and subjected to β-irradiation in the range 10-25 KGy. Exposure to radiation caused the polymer to degrade thereby resulting in a polymer with reduced molecular weight and a corresponding polymer solution with reduced viscosity. In some embodiments, the invention provides a process for preparing an injectable composition as described herein, the process comprising: a) subjecting a PLGA polymer to a sufficient amount of β-irradiation to degrade at least a portion of the polymer thereby reducing its molecular weight; and b) dissolving the polymer in a solvent to form a polymeric solution having a desired viscosity. In some embodiments, a mixture of drug and PLGA polymer are exposed to beta-irradiation prior to addition of the solvent, which would result in formation of a sterilized injectable composition of the invention.

Embodiments of the invention include those wherein: a) the molecular weight of the polymer is greater before irradiation than it is after irradiation; b) the molecular weight of the polymer is greater than 15 KDa before irradiation; c) the molecular weight of the polymer is in the range of 15-60 KDa, 25-52 KDa or 28-43 KDa after irradiation; d) the viscosity of a polymeric solution containing polymer that has not been irradiated is greater than about 0.5 Pa·s; e) the viscosity of a polymeric solution containing polymer that has been irradiated is in the range of 0.5-7.0 Pa·s, 0.5-3.0 Pa·s or 0.7 to 2.0 Pa·s; and/or f) the sufficient amount of radiation is at least 10, at least 15, at least 20 or at least 25 KGy.

In another preferred embodiment, in the injectable depot composition at least the drug and/or the biocompatible polymer of the composition have been submitted to terminal sterilization processes, preferably by irradiation in the range of 5-25 KGy.

The injectable composition is used to treat a disorder, disease or condition that is therapeutically responsive to risperidone. The invention comprises administering to a subject in need thereof an amount of injectable composition sufficient to provide therapeutic plasma levels of risperidone in the subject during the period of at least 1 to 14, at least 2 to 14 or at least 3 to 14 days after administration (the dosing period). The dosing period can exceed two weeks.

In humans, the average plasma concentration of risperidone can range from about 3-200, about 5-80, or about 10-60 ng/ml when an amount of injectable composition equivalent to a dose of about 25-150, about 37.5-125, or about 50-100 mg of risperidone is administered. The average Cmin during the dosing period is in the range of about 1-80, 5-50, or about 5-40 ng/ml when an amount of injectable composition equivalent to a dose of about 25-150, about 37.5-125, or about 50-100 mg, respectively, of risperidone is administered. The average Cmax during the dosing period is in the range of about 8-300, 10-150, or 10-120 ng/ml when an amount of injectable composition equivalent to a dose of 25-150, 37.5-125, or 50-100 mg, respectively, of risperidone is administered. Some individual subjects may, on an equivalent dose basis, exhibit plasma concentrations outside the ranges specified herein for reasons such as poor health, advanced age, compromised metabolism, renal failure, disease, etc. Even so, a majority of subjects in a patient population to which the injectable implant is administered will exhibit plasma concentrations with those specified herein.

The implant of the invention can provide substantially improved plasma levels of risperidone during the initial one to three days after administration when compared to the RISPERIDAL CONSTA injectable formulation when administered on an equivalent dose basis. The implant of the invention can provide substantially the same average plasma levels of risperidone during a full dosing period after administration when compared to the RISPERIDAL CONSTA injectable formulation when administered on an equivalent dose basis.

As used herein, whenever the plasma concentration of risperidone is mentioned, such plasma concentration includes within it the sum total of the plasma concentrations of risperidone and its metabolite(s), such as 9-OH-risperidone (paliperidone).

The plasma concentration profile during the dosing period can exhibit one, two, or more maxima and one, two or more minima. An initial maximum can be caused by dissolution of risperidone during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to three days or one to two days of the dosing period; b) the plasma profile exhibits a maximum during the latter 11 to 13 days or 12 to 14 days of the dosing period; c) the plasma profile exhibits a maximum during the initial days of the dosing period and a maximum during the remaining days of the dosing period; or d) the plasma profile is substantially level (within ±20%, ±15%, ±10% or ±5% of the average or mean) during the dosing period.

As used herein, the term "dosing period" refers to the period of days or weeks as measured from the initial day after administration to at least 14 days after administration. During the dosing period, the implant will provide therapeutic plasma levels of risperidone for at least 11 days, at least 12 days, at least 13 days, at least 14 days, at least 21 days, at least 28 days, at least 31 days or at least 36 days. A dosing period can end after expiration of a predetermined number of days or after the plasma level of risperidone drops below therapeutic levels. A dosing period of at least 4 weeks is preferred.

As used herein, a "treatment period" refers to the weeks, months or years during which implants of the invention are administered to a subject. A treatment period generally comprises plural dosing periods. Dosing periods can occur sequentially or in an overlapping manner during a treatment period. For example, a first dose of injectable composition is administered and a second dose of injectable composition can be administered within one to three weeks following administration of the first dose, such that each dose will have its own corresponding dosing period, and the dosing periods would overlap. Dosing periods will typically be sequentially or overlap by no more than one or two days.

The injectable composition can be administered to a subject in one or more injection sites on the same day and still be considered as being part of the same dosing period. For example, part of a dose can be administered to a first injection site and another part of the same dose can be administered to another injection site. A single-body implant will form at each injection site. Such a mode of administration within a same day is considered to be administration of a single dose with a single dosing period.

Alternatively, administration can be modified such that there is one point of needle entry into the subject but more than one injection site below the skin, which can be achieved by making a first penetration into the skin and muscle and administering a portion of a dose, then partially withdrawing and redirecting the needle into another section of muscle, while maintaining the tip of the needle beneath the skin, and then injecting another portion of the dose into this other section of muscle. Such a mode of administration is still considered to be administration of a single dose within a single dosing period.

The plasma concentration profile during the dosing period can exhibit one, two, or more maxima and one, two or more minima. An initial maximum can be caused by dissolution of risperidone during the initial day(s) of the dosing period followed by a slowing of the release thereof and another maximum can be caused by increased rate of release during the remaining days of the dosing period. Embodiments of the invention include those wherein: a) the plasma profile exhibits a maximum during the initial one to six days or one to three days of the dosing period; b) the plasma profile exhibits a maximum during the latter 14 to 24 days of a 4-week dosing period; c) the plasma profile exhibits a maximum during the initial days of the dosing period and a maximum during the remaining days of the dosing period; or d) the plasma profile is substantially level (within ±20%, ±15%, ±10% or ±5% of the average or mean) during the dosing period.

The implant of the invention can provide substantially improved plasma levels of drug during the initial one to three days after administration when compared to another injectable formulation (not according to the invention) containing the same drug when administered on an equivalent dose basis.

As used herein the term, "initial burst" or "initial release" refers to the addition of the plasma levels of risperidone plus those of 9-OH-risperidone, which addition is also called the "active moiety" throughout the present specification, from the moment of injection/administration of the injectable composition to a subject in need thereof until completion of the third day after the administration. For example, the drug can be risperidone and its metabolite can be paliperidone. In some embodiments, the initial period of release is within three days, within two days, within one day or within twelve hours after administration.

Acceptable plasma levels of active moiety during the initial burst phase are below 100 ng/ml in Beagle dogs and New Zealand White Rabbits when the dose of injectable composition administered is 2.5 mg/kg risperidone in dogs and 5 mg/kg risperidone in rabbits.

The following examples illustrate the invention and should not be considered as defining the full scope thereof.

COMPARATIVE EXAMPLE 1: Implantable Composition Including a Water-Insoluble Solvent (Example not According to the Invention)

In the present example, the composition of the implantable formulation was as follows:

| Ingredient | Amount (mg) |
|---|---|
| Resomer ®RG752S (polymer) | 100 |
| Risperidone | 25 |
| Benzyl benzoate (solvent) | 233.3 |

RG752S, 75:25 lactic/glycolic acid polymer (Boehringer Ingelheim)

The risperidone implantable formulation was prepared by completely dissolving the polymer in the solvent and subsequently suspending the drug in said polymeric solution to form an injectable drug suspension.

In Vitro Release Profile:

The risperidone release from the formulation of this example was evaluated according to the following procedure. The amount of formulation corresponding to 25 mg of risperidone was injected from prefilled syringes having 21 G needles into flasks having a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer and the amount of risperidone present in the sample was determined by UV spectrophotometry. The profile of risperidone released from the implants of this example is shown in FIG. 1. The results are expressed as % Risperidone released from implants as a function of time.

As depicted in FIG. 1, the release of risperidone during the first 24 hours is close to 20% of the injected amount and close to 50% in the first 48 hours. This finding is not in accordance with previous teachings such as U.S. Pat. No. 6,673,767, since this low water-miscible solvent is clearly unable to control the initial diffusion of risperidone from the polymer matrix.

In Vivo Plasma Levels after Intramuscular Administration to New Zealand Rabbit:

The risperidone composition of this example was injected intramuscularly to New Zealand White rabbits weighing an average of 3 kg. The amount injected corresponded to a dose of 15 mg risperidone, and the composition was injected intramuscularly into the left hind leg using a syringe equipped with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d and 28 d.

Figure 2:
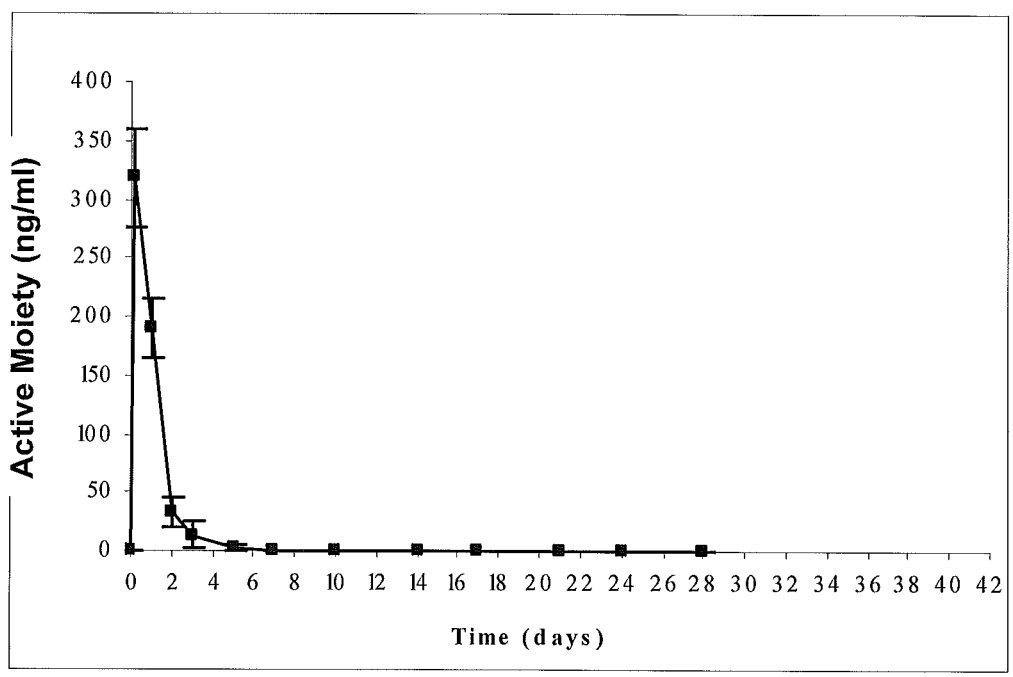
FIG. 2: In vivo plasma levels of risperidone plus 9-OH-risperidone following injection of the composition of Comparative Example 1 (risperidone, polymer and a water-insoluble solvent) in rabbits.

The kinetics of the plasma levels corresponding to the risperidone active moiety was evaluated by measuring both risperidone and its active metabolite 9-OH-risperidone in the plasma samples. The profile of the plasma levels of the risperidone active moiety is shown in FIG. 2. The results are expressed as the addition of risperidone plus 9-OH-risperidone concentrations (ng/ml) as the function of time, since the therapeutic activity of 9-OH-risperidone is substantially equivalent to that of risperidone. As depicted in FIG. 2, the injection of an amount of composition equivalent to 15 mg risperidone to New Zealand White rabbits resulted in very high initial plasma levels followed by a rapid decrease, with no significant plasma levels from day 3 onwards. All 3 animals exhibited severe adverse effects related to the very high plasma levels of risperidone active moiety 15 min after the injection, which demonstrates the rather poor control on the initial drug release achieved with this composition.

EXAMPLE 1: Study of Different Water-Soluble Solvents with Different Dipole Moment In the present example, the composition of the implantable formulation was as follows:

| Ingredient | Composition 1 Amount (mg) | Composition 2 Amount (mg) | Solvent dipole moment (D) |
|---|---|---|---|
| Resomer ®RG503 (polymer) | 100 | 100 | |
| Risperidone | 25 | 25 | |
| Dimethyl sulfoxide (solvent) | 233.3 | — | 3.96 |
| 1,4-dioxane (solvent) | — | 233.3 | 0.45 |

RG503, 50:50 lactic/glycolic acid polymer (Boehringer Ingelheim)

The risperidone-implantable formulation was prepared by completely dissolving the polymer in either of the cited water-miscible solvents having different dipole moment (DMSO or 1,4-dioxane) and subsequently suspending the drug in said polymeric solution.

In Vitro Release Profile:

The risperidone release from the formulations of this example was evaluated according to the following procedure: the amount of formulation corresponding to 25 mg of risperidone was injected from prefilled syringes equipped with 21 G needles into flasks followed by careful addition of a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer, and the amount of risperidone amount present in the sample was determined by UV spectrophotometry.

Figure 3:
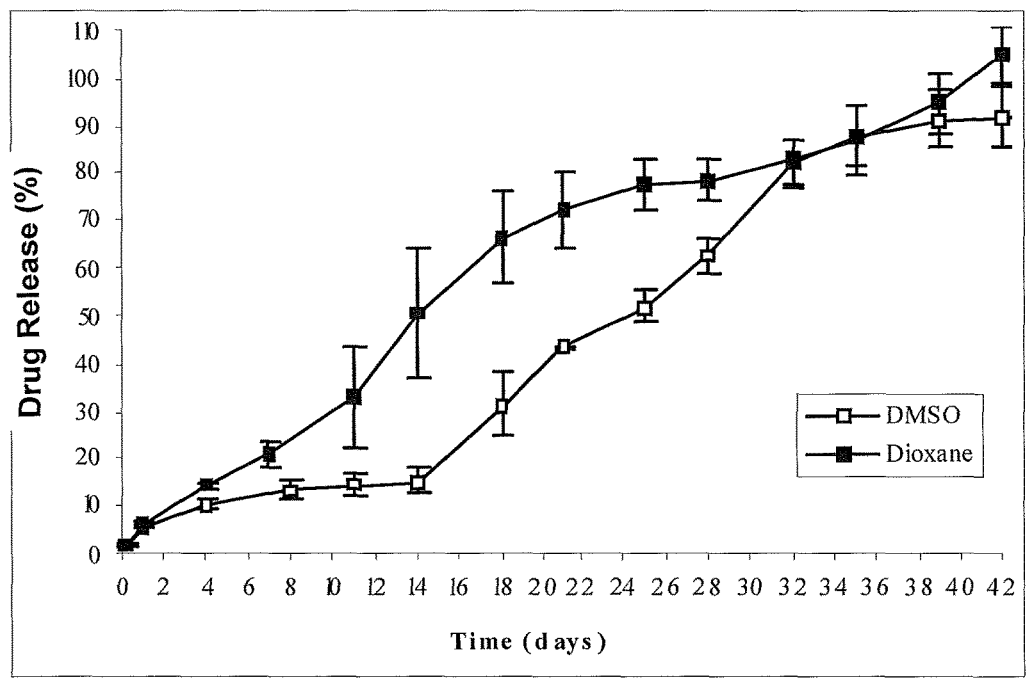
FIG. 3: In vitro release profile of risperidone for the composition of Example 1 (risperidone, polymer and water-soluble solvents having different dipole moment).

The profile of the risperidone released from the formulations is shown in FIG. 3. The results are expressed as % Risperidone released from the implants as a function of time. As depicted in FIG. 3, and in comparison with FIG. 1 (corresponding to Comparative Example 1), the use of water miscible solvents versus water-immiscible solvents in the implantable compositions of the invention allows for a more precise control of the initial release of risperidone from the polymer matrix. The present example also shows the influence of the dipole moment of the solvent in the release of risperidone from the implantable compositions of the invention: The use of solvents with lower dipole moment (dioxane) causes a higher risperidone initial diffusion than solvents having higher dipole moment solvents (DMSO) about 3.9-4.3 D, which solvents notably reduce the drug diffusion during 2 weeks.

EXAMPLE 2: Study of Solvents with a High Solubility for Risperidone

In the present example, the composition of the implantable formulation was as follows:

| Ingredient | Amount (mg) |
| --- | --- |
| Resomer®RG752S (polymer) | 100 |
| Risperidone | 25 |
| Benzyl alcohol (solvent) | 233.3 |

RG752S, 75:25 lactic/glycolic acid polymer (Boehringer Ingelheim)

The risperidone-implantable formulation of this example was prepared by completely dissolving the polymer in the water-miscible solvent having a high solubility for risperidone (benzyl alcohol) and subsequently suspending the drug in said polymeric solution.

In Vitro Release Profile:

The release of risperidone from the formulation was evaluated according to the following procedure: the amount of formulation corresponding to 25 mg of risperidone was injected from prefilled syringes equipped with a 21 G needle into flasks having a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer, and the amount of risperidone present in the sample was determined by UV spectrophotometry.

Figure 4:
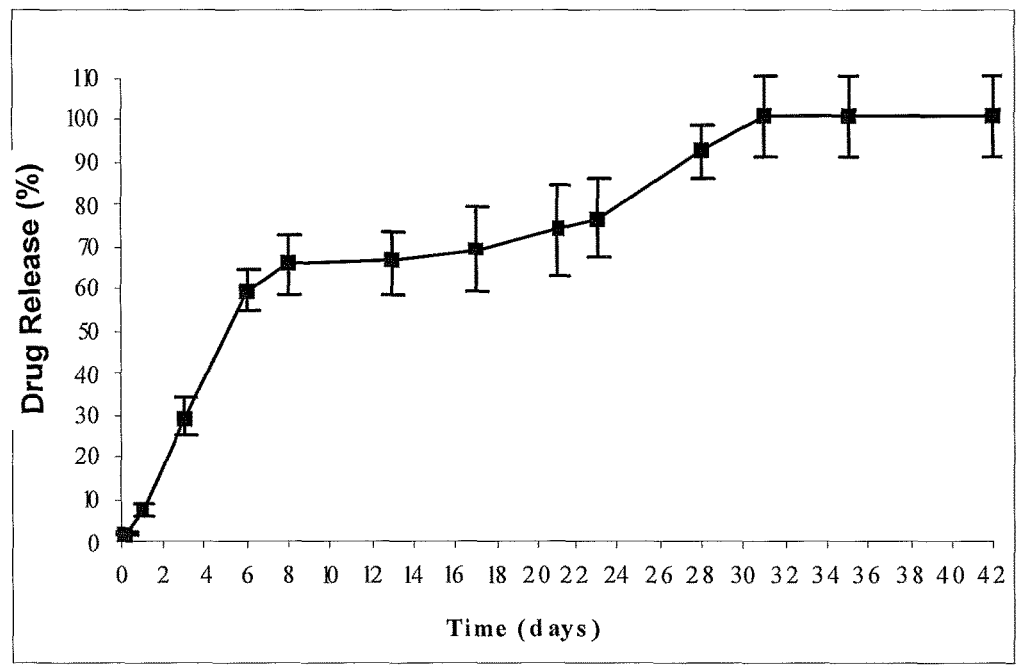
FIG. 4: In vitro release profile of risperidone for the composition of Example 2 (risperidone, polymer and a water-soluble solvent having a high solubility for risperidone).

The profile of risperidone released from the formulation is shown in FIG. 4. The results are expressed as % Risperidone released from the implants as a function of time. As depicted in FIG. 4, the use of solvents having a high solubility for risperidone as in the present example results in a high initial risperidone diffusion and a drug release from the polymer matrix close to 30% in the first 3 days and along the first week.

In Vivo Plasma Levels after Intramuscular Administration to New Zealand Rabbit

The risperidone composition of this example was injected intramuscularly into New Zealand White rabbits weighing an average of 3 kg. The amount injected corresponded to a dose of 15 mg risperidone and the composition was placed intramuscularly in the left hind leg using a syringe with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d and 28 d.

Figure 5:
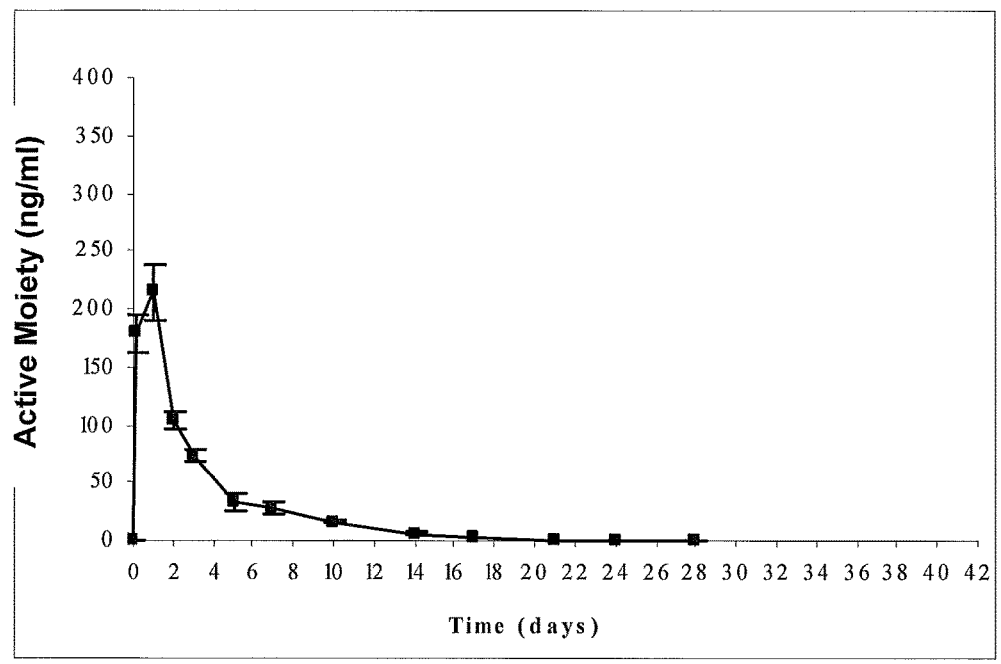
FIG. 5: In vivo plasma levels of risperidone plus 9-OH-risperidone following injection of the composition of Example 2 (risperidone, polymer and a water-soluble solvent having a high solubility for risperidone) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is depicted in FIG. 5. The results are expressed as the addition of the risperidone plus 9-OH-risperidone concentrations (ng/ml) as the function of time, since the therapeutic activity of 9-OH-risperidone is substantially equivalent to that of risperidone. As depicted in the figure, the injection of the tested composition in an amount equivalent to 15 mg risperidone to New Zealand White rabbits resulted in very high initial plasma levels followed by a rapid decrease, with no significant plasma levels from day 5 onwards. All 3 animals exhibited adverse effects related to the very high plasma levels of risperidone active moiety 15 min after the injection, which demonstrates the very poor control on the initial drug release achieved with this composition, which comprises a solvent having a high solubility for risperidone.

EXAMPLE 3: Study of Solvents with Different Solubility for Risperidone

In the present case, the risperidone implantable formulation was prepared by completely dissolving the polymer Resomer® RG503 (RG503, 50:50 lactic/glycolic acid, Boehringer Ingelheim) in different solvents (NMP, PEG and DMSO) in which risperidone exhibits intermediate to low solubility (in all cases below 65 mg/ml) and subsequently suspending the risperidone in the respective solvent.

| Ingredient | Composition 1 (DMSO) Amount (mg) | Composition 2 (NMP) Amount (mg) | Composition 3 (PEG300) Amount (mg) |
| --- | --- | --- | --- |
| Risperidone | 25 | 25 | 25 |
| Resomer ®RG503 (polymer) | 100 | 100 | 66.6 |
| DMSO | 233.3 | — | — |
| NMP | — | 233.3 | — |
| PEG | — | — | 266.7 |

Risperidone solubility: 62.5 mg/mL in NMP; 9.5 mg/mL in DMSO; 8.2 mg/mL in PEG300

In Vitro Release Profile:

The risperidone release from the formulations of this example was evaluated according to the following procedure: the amount of formulation corresponding to 25 mg of risperidone was injected from prefilled syringes equipped with a 21 G needle into flasks followed by the careful addition of a pre-warmed release medium. The release medium was 250 ml phosphate buffer pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer, and the amount of risperidone present in the sample was determined by UV spectrophotometry.

Figure 6:
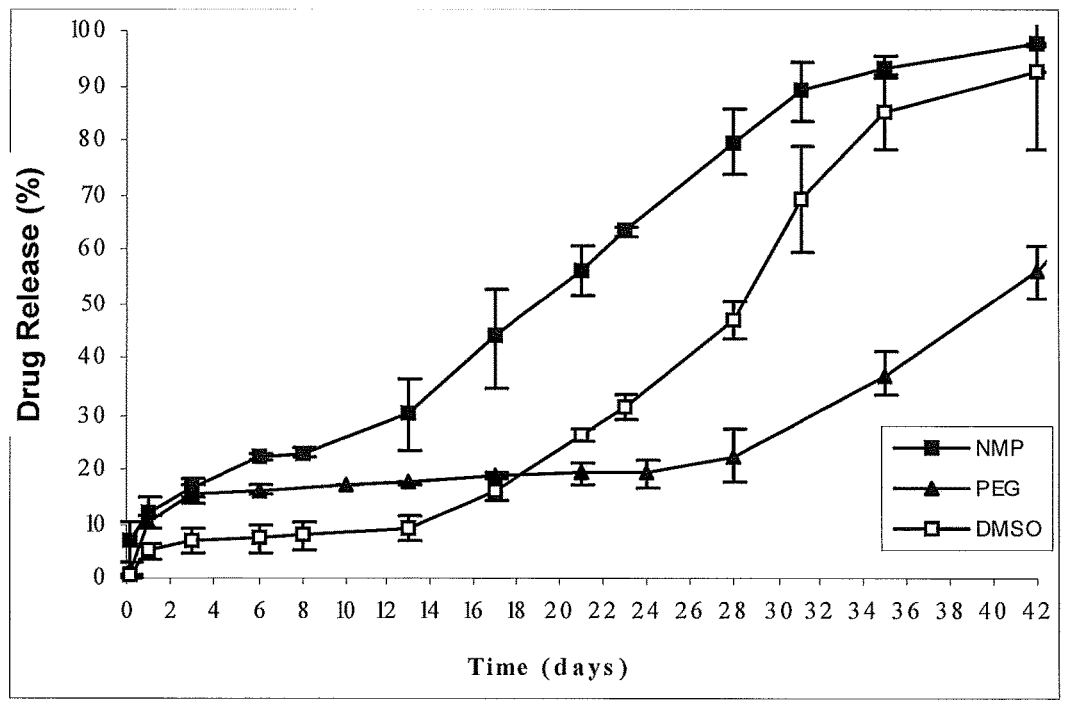
FIG. 6: In vitro release profile of risperidone for the composition of Example 3 (risperidone, polymer and water-soluble solvents having moderate to low solubility for risperidone).

The profile of risperidone released from the formulations is shown in FIG. 6. The results are expressed as % Risperidone released from the formulations as a function of time. As depicted in FIG. 6, the use of a solvent having a lower risperidone solubility (in comparison to high solubility as in FIG. 4 from Example 2) offers initial controlled risperidone diffusion from the polymer matrix and a controlled release up to at least 28 days. Hence, the use of solvents having a low solubility for risperidone, such as DMSO, as in the present example, allows a more precise control of the drug released during the solvent diffusion and the polymer precipitation.

EXAMPLE 4: Study of Different Polymer Concentrations with Respect to the Solvent In the present example, the compositions of the implantable formulations were as follows:

|  | Composition 1 | Composition 2 | Composition 3 | Composition 4 |
|---|---|---|---|---|
| Ingredient | Amount (mg) | | | |
| Risperidone | 25 | 25 | 25 | 25 |
| Resomer ®RG503 (polymer) | 33.3 | 66.5 | 100 | 190 |
| Dimethyl sulfoxide (solvent) | 300 | 266.8 | 233.3 | 285 |
| Polymer concentration | (%, w/w respect to polymer + solvent) | | | |
|  | 10 | 20 | 30 | 40 |

RG503, 50:50 lactic/glycolic acid (Boehringer Ingelheim)

The above values are otherwise expressed as follows:

| Ingredient | Composition 1 | Composition 2 | Composition 3 | Composition 4 |
|---|---|---|---|---|
|  | Amount (%) | | | |
| Resomer ®RG503 (polymer) | 10 | 20 | 30 | 40 |
| Dimethyl sulfoxide (solvent) | 90 | 80 | 70 | 60 |

The risperidone-implantable formulations were prepared by completely dissolving the polymer in the solvent in different proportions and subsequently suspending the drug in said polymeric solution.

In Vitro Release Profile:

The risperidone release from the formulations of this example was evaluated according to the following procedure: the amount of formulation corresponding to 25 mg of risperidone was injected from prefilled syringes by using a 21 G needle into flasks followed by the careful addition of a pre-warmed release medium. The release medium was 250 ml phosphate buffer at pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer, and the amount of risperidone present in the sample was determined by UV spectrophotometry.

Figure 7:
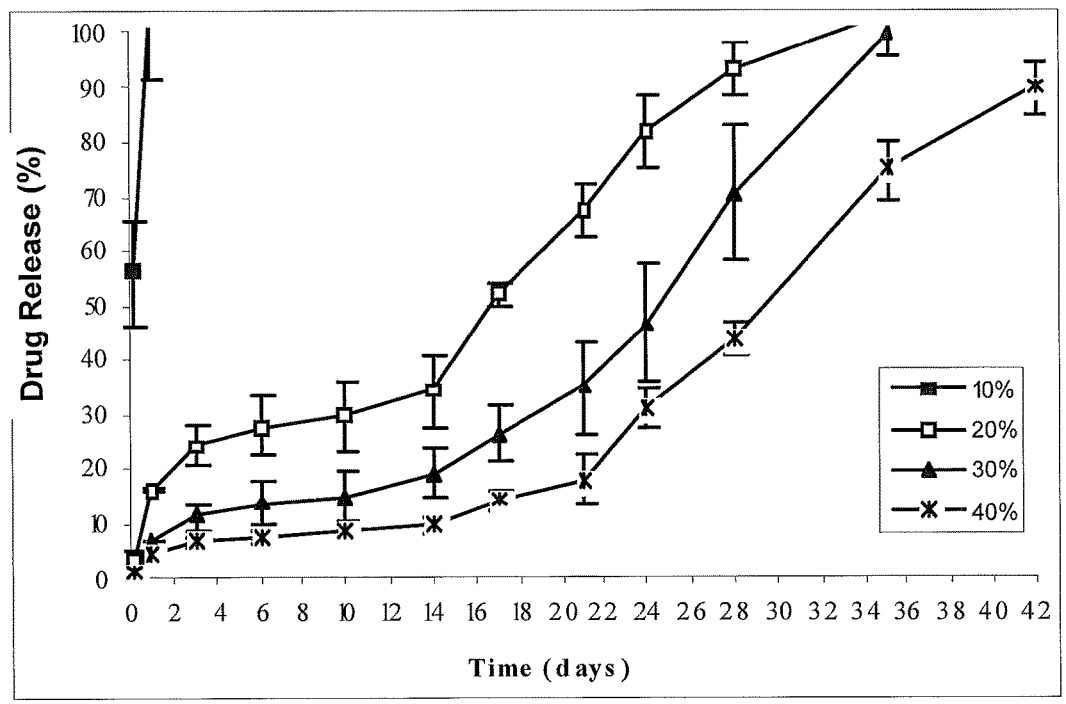
FIG. 7: In vitro release profile of risperidone for the compositions of Example 4 (different polymer concentrations with respect to solvent, DMSO).

The profile of risperidone released from the formulations of this example is shown in FIG. 7. The results are expressed as % Risperidone released from the formulations as a function of time. As it can be observed in FIG. 7, the use of polymer matrix solutions having a low polymer concentration (10% w/w), produces an extremely high initial risperidone release, so that the control of risperidone diffusion is very difficult. Although an increase in the polymer concentration to 20% (w/w) notably improves the capacity to control the risperidone released from the polymer matrix, it is still not enough to completely control the initial risperidone diffusion release, which is close to 15% during first 24 hours. Polymer concentrations at 30 and 40% (w/w) lead to an efficient initial drug release control, achieving controlled release profiles up to 35-42 days.

EXAMPLE 5: Study of a Low (10%) Polymer Concentration with Respect of the Solvent, where the Solvent has a Very High Solubility for Risperidone In the present example, the composition of the implantable formulation was as follows:

| Ingredient | Amount (mg) |
|---|---|
| Resomer ®RG752S (polymer) | 100 |
| Risperidone | 25 |
| Benzyl alcohol (solvent) | 900 |

RG752S, 75:25 lactic/glycolic acid polymer (Boehringer Ingelheim)

The risperidone-implantable formulation was prepared by completely dissolving the polymer in a solvent having a very high solubility for risperidone (benzyl alcohol) and subsequently suspending the drug in said polymeric solution. The concentration of the polymer with respect to the solvent was low (10%).

In Vitro Release Profile:

The risperidone release from the formulation of this example was evaluated according to the following procedure: the amount of formulation corresponding to 25 mg of risperidone was injected from prefilled syringes equipped with a 21 G needle into flasks having a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, 3 d, 6 d, 8 d, 10 d, 13 d, 17 d, 21 d, 23 d, 28 d, 31 d, 35 d, 42 d), 5 ml of release medium was collected and replaced with fresh buffer, and the amount of risperidone present in the sample was determined by UV spectrophotometry.

Figure 8:
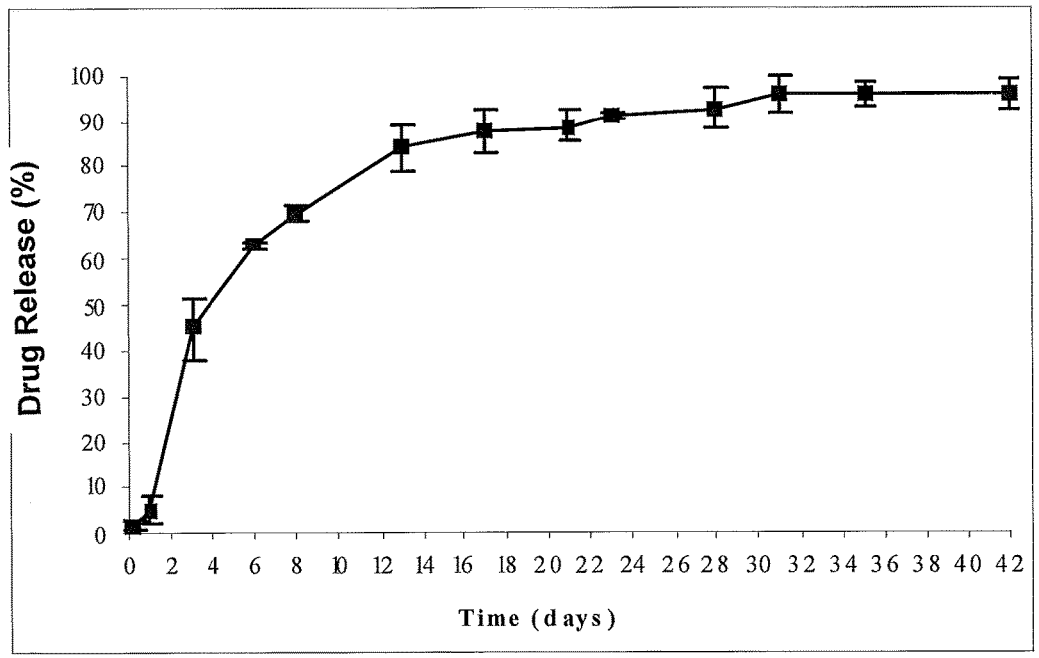
FIG. 8: In vitro release profile of risperidone for the compositions of Example 5 (low polymer concentration of a solvent having a high solubility for risperidone).

The profile of risperidone released from the implants is shown in FIG. 8. The results are expressed as % Risperidone released from the formulation as a function of time. As depicted in FIG. 8, and in line with the results shown in FIG. 7 from Example 4, a concentration of the polymer of 10% (w/w) in the polymeric solution is not enough to retain the risperidone in the implantable formulations, therefore providing an initial release of risperidone that is too high during the first days.

In Vivo Plasma Levels after Intramuscular Administration to New Zealand Rabbit

The risperidone composition was injected intramuscularly to New Zealand White rabbits weighing an average of 3 kg. The amount injected corresponded to a dose of 15 mg risperidone and the composition was placed intramuscularly into the left hind leg using a syringe with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d and 28 d.

Figure 9:
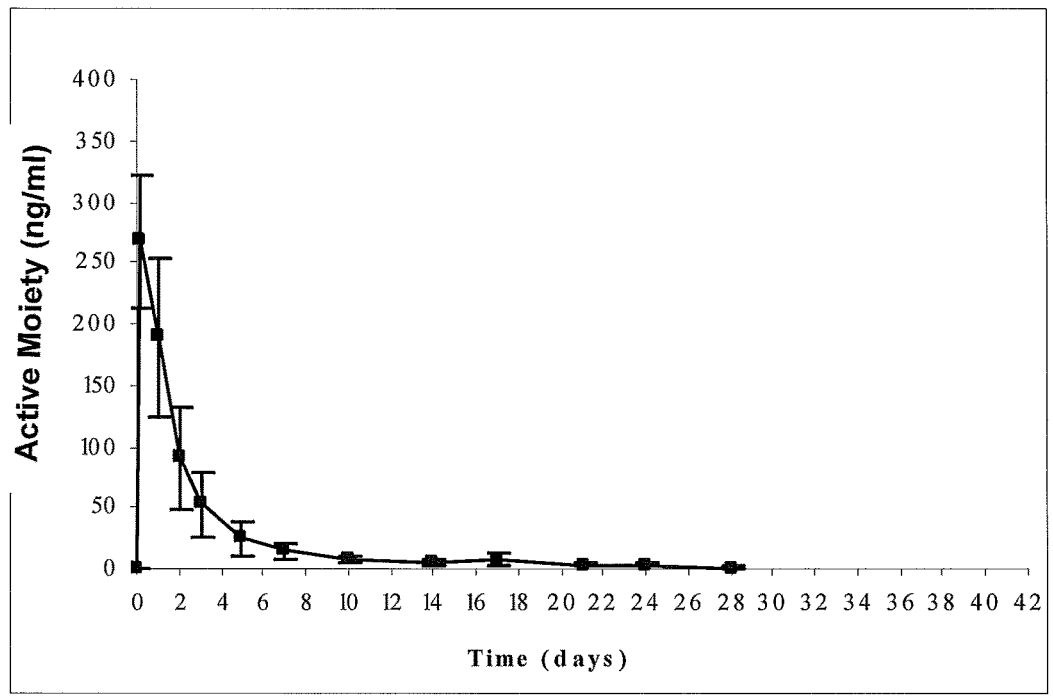
FIG. 9: In vivo plasma levels of risperidone plus 9-OH-risperidone following injection of the composition of Example 5 (low polymer concentration of a solvent having a high solubility for risperidone) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 9. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation equivalent to 15 mg risperidone to New Zealand White rabbits resulted in very high initial plasma levels of risperidone, followed by a rapid decrease, with no significant plasma levels from day 5 onwards. All 3 animals exhibited adverse effects related to the very high plasma levels of risperidone active moiety 15 min after the injection, which shows a very poor control on the initial drug release achieved with this composition comprising low polymer concentration in the polymer matrix.

EXAMPLE 6: Study of Intermediate (25%) Polymer Concentrations with Respect to Solvent In the present example, the compositions of the implantable formulation were as follows:

| Ingredient | Amount (mg) |
| --- | --- |
| Resomer ®RG503 (polymer) | 41.7 |
| Risperidone | 25 |
| Polyethylene glycol 300 (solvent) | 125 |

RG503, 50:50 lactic/glycolic acid polymer (Boehringer Ingelheim)

The risperidone-implantable formulations were prepared by completely dissolving the polymer in the solvent and subsequently suspending the drug in the polymeric solution. The concentration of the polymer with respect to the solvent was intermediate (25%).

In Vivo Plasma Levels after Intramuscular Administration to New Zealand Rabbit

The risperidone composition was injected intramuscularly into New Zealand White rabbits weighing an average of 3 kg. The amount injected corresponded to a dose of 15 mg risperidone and the composition was placed intramuscularly in the left hind leg using a syringe with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 10:
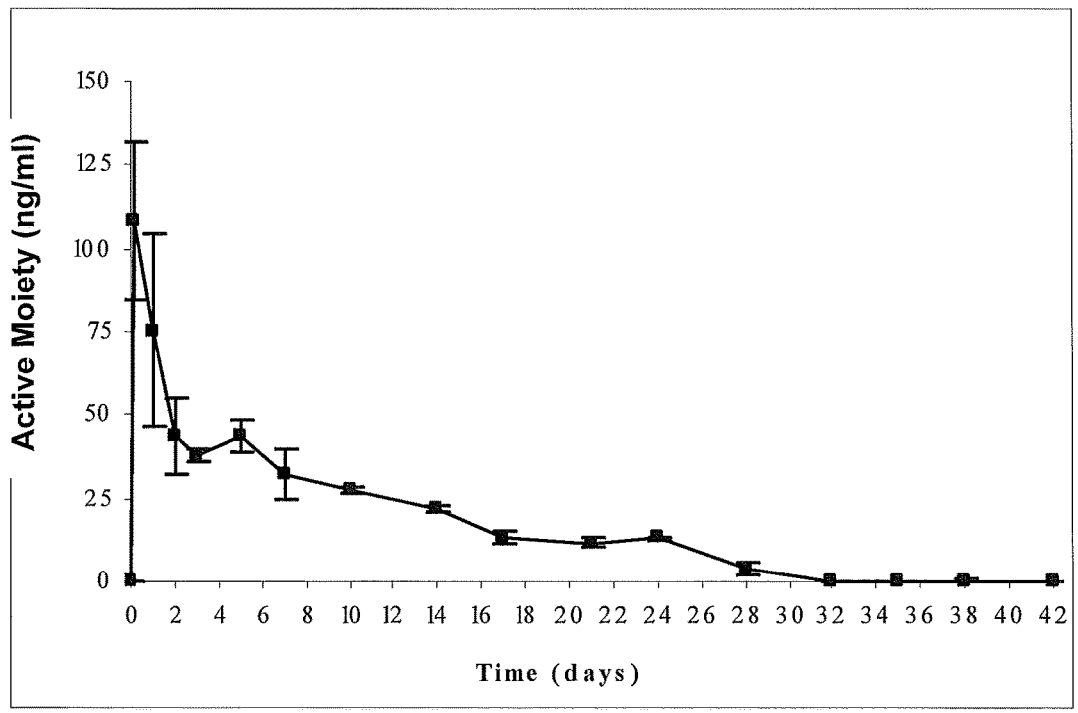
FIG. 10: In vivo plasma levels of risperidone plus 9-OH-risperidone following injection of the composition of Example 6 (intermediate polymer concentration with respect to solvent) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 10. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation equivalent to 15 mg risperidone to New Zealand White rabbits resulted in moderate initial plasma levels followed by a decrease until day 2 and sustained plasma levels at least up to 24 days. The results obtained in this example are in accordance with those from Example 4, where polymer concentrations of 20% (w/w) or higher with respect to the polymeric solution are able to control the initial risperidone diffusion and achieve prolonged release over time.

EXAMPLE 7: Study of Different Drug Loadings

The risperidone implantable formulation of this example was prepared by completely dissolving polymer Resomer® RG503 (RG503, 50:50 lactic/glycolic acid, Boehringer Ingelheim) in DMSO and subsequently dispersing the drug in the appropriate amount to obtain a final drug loading between 7-13% (w/w) (weight of risperidone in respect of the total composition weight).

| | Composition drug loading | |
| --- | --- | --- |
| | 7% | 13% |
| Ingredient | Amount (mg) | |
| Risperidone | 15 | 15 |
| Resomer ®RG503 (polymer) | 60 | 30 |
| DMSO | 140 | 70 |

In Vivo Plasma Levels after Intramuscular Administration to New Zealand Rabbit

The risperidone formulation of this example was injected intramuscularly into New Zealand White rabbits weighing an average of 3 kg. The amount injected corresponded to a dose of 15 mg risperidone and the composition was placed intramuscularly in the left hind leg using a syringe with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 11:
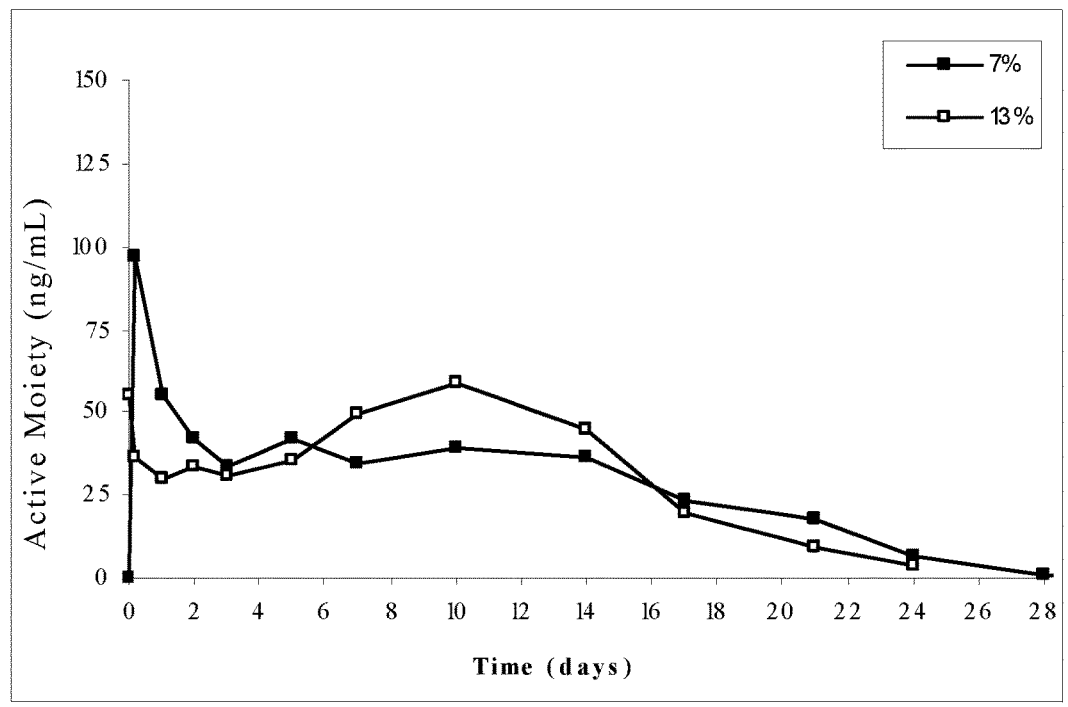
FIG. 11: In vivo plasma levels of risperidone plus 9-OH-risperidone following injection of the compositions of Example 7 (different drug loadings) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 11. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of composition equivalent to 15 mg risperidone to New Zealand White rabbits resulted in moderate and controlled initial plasma levels. An increase in the drug loading is related to a lower initial drug diffusion and release, producing as a result a decrease in the initial plasma levels. Therefore, a high drug loading is preferable for the case of long-term formulations, in order to achieve better balanced plasma levels in the whole drug release period. In general terms, a preferred range for the drug loading is between 4 and 16%, and a more preferred range is between 7 and 13%, expressed as the weight percent of drug with respect to the total composition.

EXAMPLE 8: Study of Different Particle Sizes

In the present example, the following compositions of implantable formulations according to the invention were tested:

Composition A:

| Ingredient | Amount (mg) |
| --- | --- |
| Resomer ®RG503 (polymer) | 100 |
| Risperidone | 25 |
| Dimethyl sulfoxide (solvent) | 233.3 |

Composition B:

| Ingredient | Amount (mg) |
| --- | --- |
| Resomer ®RG503 (polymer) | 50 |
| Risperidone | 25 |
| Dimethyl sulfoxide (solvent) | 166.7 |

RG503, 50:50 lactic/glycolic acid polymer (Boehringer Ingelheim)

The risperidone-implantable formulations were prepared by completely dissolving the polymer in the solvent and subsequently suspending the drug in said polymeric solution. The following different risperidone particle size distributions were evaluated for the same formulation:
- 25-350 microns: d0.1, 25 microns and d0.9, 350 microns (not more than 10% of drug particles with a particle size smaller than 25 microns, and not more than 10% particles larger than 350 microns).
- 25-225 microns: d0.1 of 25 microns and d0.9 of 225 microns (not more than 10% of drug particles with a particle size smaller than 25 microns, and not more than 10% particles larger than 225 microns).
- 90-150 microns: sieved between 90-150 microns
- 45-90 microns: sieved between 45-90 microns
- milled, <10 microns: drug milled to d0.9 10 microns (not more than 10% particles larger than 10 microns).

In Vitro Release Profile:

The risperidone release from the formulations corresponding to Composition B was evaluated according to the following procedure: the amount of formulation corresponding to 25 mg of risperidone was injected from prefilled syringes equipped with a 21 G needle into flasks followed by the careful addition of a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, and periodically up to a maximum of 35 d), 5 ml of release medium was collected and replaced with fresh buffer, and the amount of risperidone present in the sample was determined by UV spectrophotometry.

Figure 12:
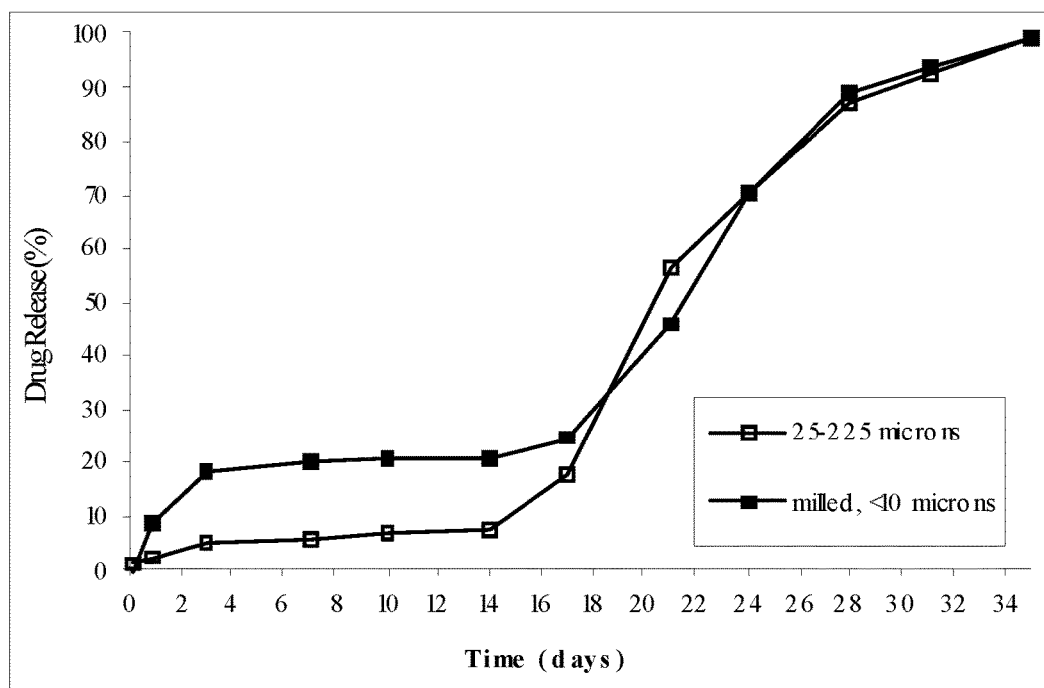
FIG. 12: In vitro release profile of risperidone for Composition B of Example 8 (different particle sizes).

The profile of risperidone released from the implants of this example is shown in FIG. 12. Results are expressed as % Risperidone released from the implants as a function of time. As depicted in FIG. 12, the small drug particles (less than 10 microns) favoured the in vitro drug diffusion during first days following administration of the implantable formulation, whereas the use of a mixture of particle sizes, comprising larger and smaller particles, reduced the initial diffusion. Accordingly, in some embodiments, the risperidone comprises a broad particle size distribution, which can be monomodal, bimodal or trimodal.

In Vivo Plasma Levels after Intramuscular Administration to New Zealand Rabbit

The risperidone formulations corresponding to Compositions A and B of this example were injected intramuscularly into New Zealand White rabbits weighing an average of 3 kg. The amount injected corresponded to a dose of 15 mg risperidone and the composition was placed intramuscularly in the left hind leg using a syringe equipped with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 13:
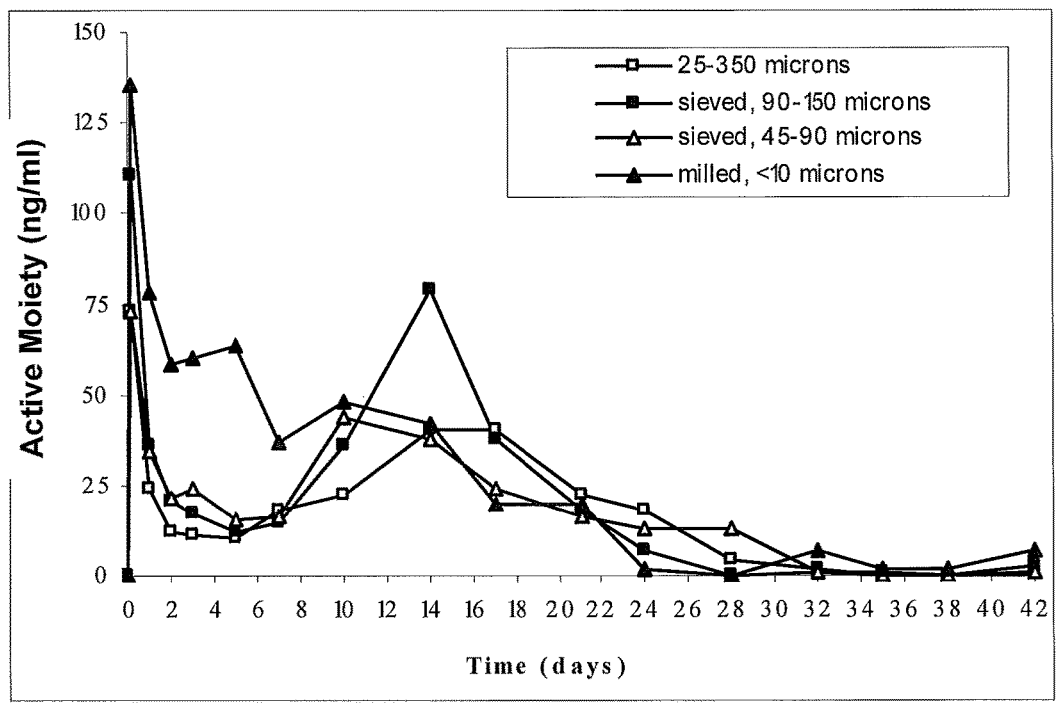
FIG. 13: In vivo plasma levels of risperidone plus 9-OH-risperidone following injection of Composition A of Example 8 (different particle sizes) in rabbits.
Figure 14:
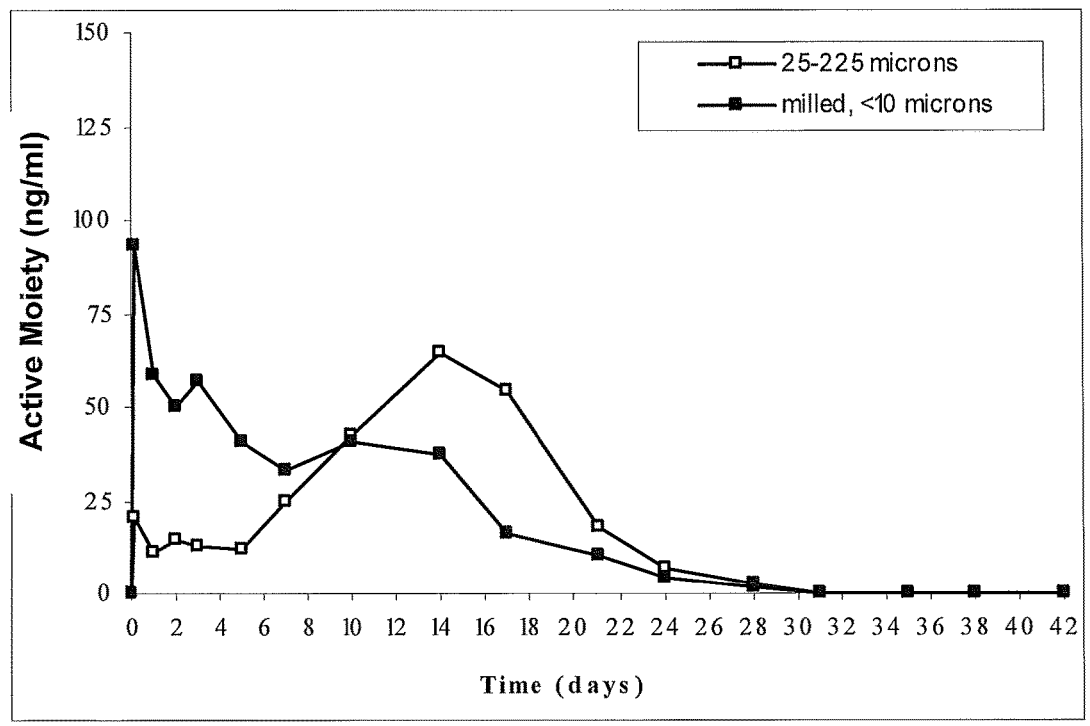
FIG. 14: In vivo plasma levels of risperidone plus 9-OH-risperidone following injection of Composition B of Example 8 (different particle sizes) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIGS. 13 and 14 for Compositions A and B, respectively. The results are expressed as the addition of the risperidone plus 9-OH-risperidone concentrations (ng/ml) as a function of time, since the therapeutic activity of 9-OH-risperidone is substantially equivalent to that of risperidone. As depicted in the figures, the injection of an amount of formulation of the Compositions A and B corresponding to an equivalent to 15 mg risperidone to New Zealand White rabbits resulted in moderate and controlled initial plasma levels followed by significant plasma levels up to at least 21 days. The smaller particle sizes produce an initial raise in the plasma levels and shorten the therapeutic plasma levels window. The use of higher particle sizes, thus avoiding smaller ones, resulted in a dramatic reduction of the initial burst effect by decreasing drug diffusion and subsequent delay in drug release until the polymer matrix degrades. As depicted in FIG. 14, the use of a controlled mixture of drug particle sizes provided a more controlled initial release during the diffusion phase, followed by an increase in plasma levels once the polymer degradation begins.

In Vivo Plasma Levels after Intramuscular Administration to Beagle Dog

The risperidone formulations of Composition B of this example were intramuscularly injected to Beagle dogs weighing an average of 10 kg. The amount injected corresponded to a dose of 25 mg risperidone and the composition was intramuscularly placed in the left hind leg using a syringe with a 20 G needle. Total number of dogs was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 15:
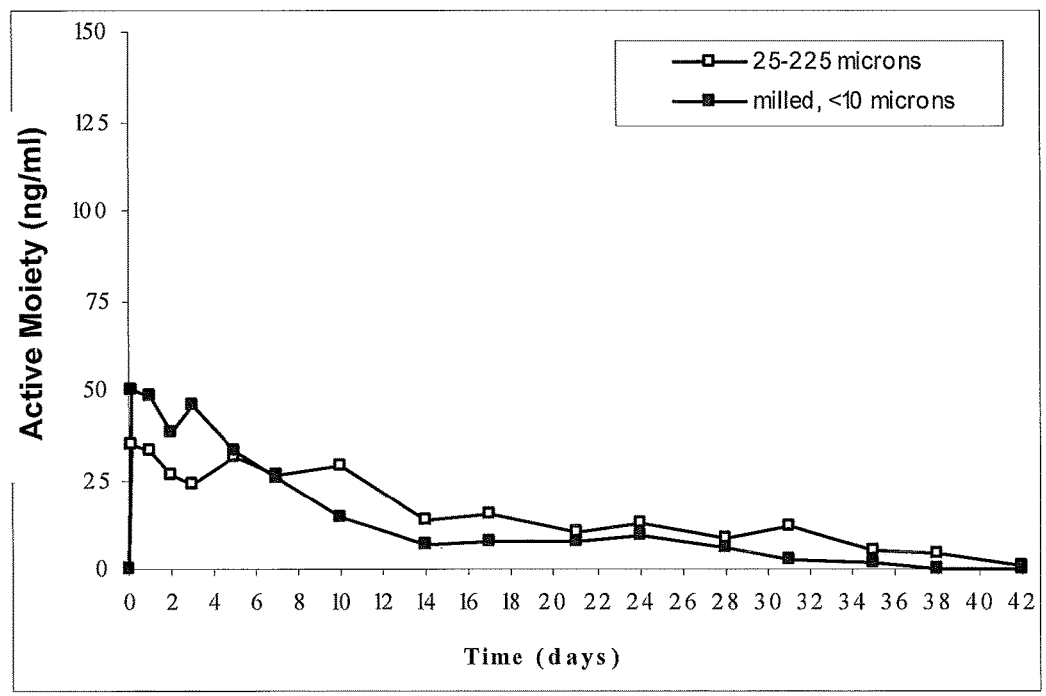
FIG. 15: In vivo plasma levels of risperidone plus 9-OH-risperidone following injection of Composition B of Example 8 (different particle sizes) in dogs.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 15. The results are expressed as the addition of the risperidone plus 9-OH-risperidone concentrations (ng/ml) as a function of time, since the therapeutic activity of 9-OH-risperidone is substantially equivalent to that of risperidone.

The injection of risperidone formulations corresponding to Composition B of this example in an amount equivalent to 25 mg risperidone to Beagle dogs resulted in controlled initial plasma levels followed by significant plasma levels up to at least 28 days as it can be observed in FIG. 15. As previously noted in relation to the intramuscular administration of Composition B to rabbits (FIGS. 13 and 14), the administration of the same composition to dogs revealed the same variable effect depending on drug particle size: Small particles (<10 microns) induced higher initial plasma levels and a relatively fast decrease in comparison with mixtures of particles sizes comprising both small and large particles (25-225 microns), which combination is able to reduce the initial plasma levels and favours a more sustained plasma level along time.

EXAMPLE 9: Study of the Viscosity of the Polymeric Solution

The risperidone-implantable formulations of this example were prepared by completely dissolving the polymer in DMSO or NMP as the solvent and subsequently suspending the drug in said polymeric solution. The formulations were the following in order to achieve polymeric solutions having different viscosities:

| Ingredient (mg) | | | Polymer (%, w/w on polymeric (polymer + solvent) solution) | Viscosity of the polymeric solution (Pa · s) |
|---|---|---|---|---|
| Risperidone | Polymer (type) | Solvent (type) | | |
| 25 | 33.3 (Resomer ®RG503) | 300 (DMSO) | 10 | 0.03 |
| 15 | 60 (Resomer ®RG752S) | 140 (NMP) | 30 | 0.10 |
| 25 | 66.5 (Resomer ®RG503) | 266.8 (DMSO) | 20 | 0.18 |
| 15 | 60 (Resomer ®RG752S) | 90 (DMSO) | 40 | 0.43 |
| 15 | 30 (Resomer ®RG753S) | 70 (DMSO) | 30 | 0.66 |
| 15 | 60 (Resomer ®RG503) | 140 (DMSO) | 30 | 1.12 |
| 15 | 60 (Resomer ®RG503) | 111.5 (DMSO) | 35 | 2.73 |
| 15 | 60 (Resomer ®RG504) | 140 (DMSO) | 30 | 6.12 |
| 15 | 60 (Resomer ®RG503) | 90 (DMSO) | 40 | 6.77 |
| 25 | 33.3 (Resomer ®RG503) | 300 (DMSO) | | |

RG752S, and RG753S, 75:25 lactic/glycolic acid polymer (Boehringer Ingelheim)
RG503 and RG504, 50:50 lactic/glycolic acid polymer (Boehringer Ingelheim)

The above formulations can be otherwise expressed as follows.

| Polymer Type | Polymer (% w/w with regard to polymer + solvent) | Viscosity of the polymeric solution (Pa · s) |
|---|---|---|
| Resomer ®RG503 | 10 | 0.03 |
| Resomer ®RG752S | 30 | 0.10 |
| Resomer ®RG503 | 20 | 0.18 |
| Resomer ®RG752S | 40 | 0.43 |
| Resomer ®RG753S | 30 | 0.66 |
| Resomer ®RG503 | 30 | 1.12 |
| Resomer ®RG503 | 35 | 2.73 |
| Resomer ®RG504 | 30 | 6.12 |
| Resomer ®RG503 | 40 | 6.77 |

In Vitro Release Profile:

The risperidone release from the formulations was evaluated according to the following procedure: the amount of formulation corresponding to 25 mg of risperidone was injected from prefilled syringes equipped with a 21 G needle into flasks followed by the careful addition of a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, and periodically up to a maximum of 42 d), 5 ml of release medium was collected and replaced with fresh buffer, and the amount of risperidone present in the sample was determined by UV spectrophotometry.

Figure 16:
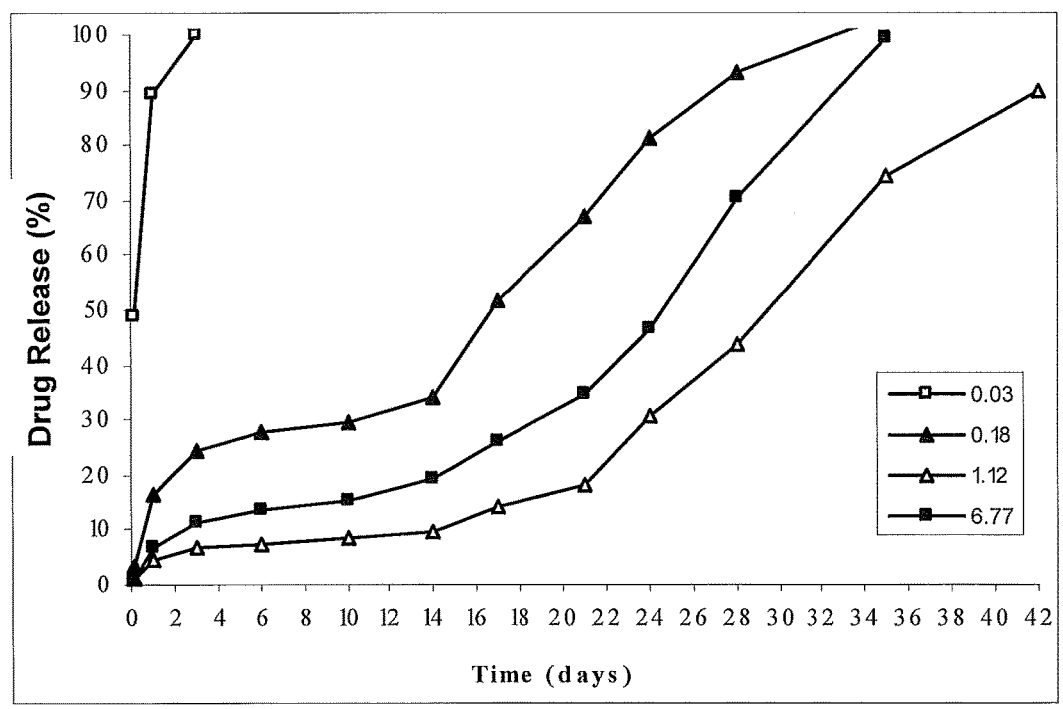
FIG. 16: In vitro release profile of risperidone for the compositions of Example 9 (different viscosities of the polymeric solution).

The profile of risperidone released from the implants of this example is shown in FIG. 16. Results are expressed as % Risperidone released from the implants as a function of time. As depicted in FIG. 16, the low polymer solution viscosities lead to completely uncontrollable (0.03 Pa·s) and fast and high initial diffusion (0.18 Pa·s) of risperidone. On the other hand, polymer solution viscosities in the range 1.12-6.77 Pa·s resulted in well-controlled in vitro drug diffusion during first days following administration of the implantable formulation, followed by moderate drug release rates up to 35-42 days.

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 3.

After injection, plasma levels were obtained at 0, 4 h, 1 d, 2 d, 3 d, 5 d, 7 d, 10 d, 14 d, 17 d, 21 d, 24 d, 28 d.

Figure 17:
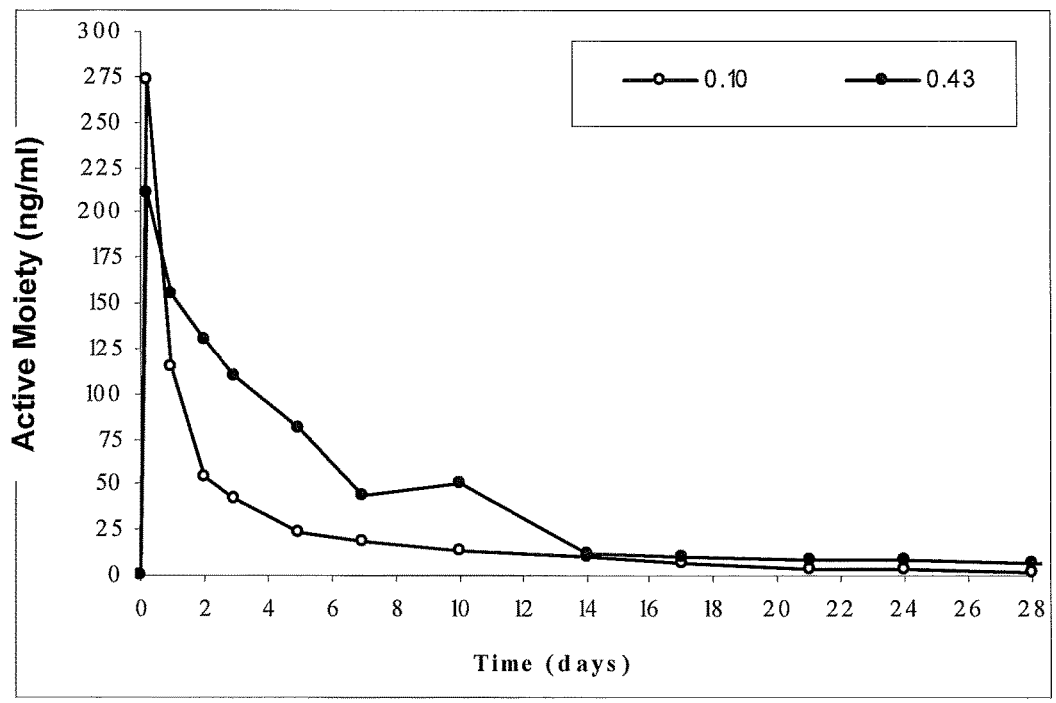
FIG. 17: In vivo plasma levels of risperidone plus 9-OH-risperidone following injection of the compositions of Example 9 (different viscosities of the polymeric solution) in rabbits.
Figure 18:
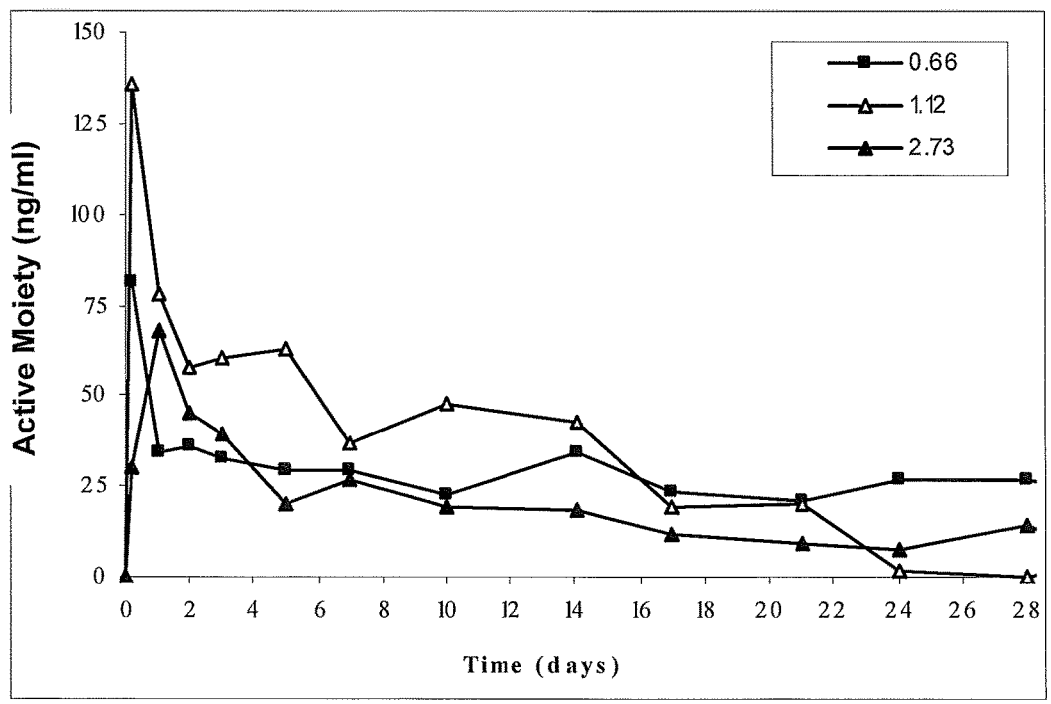
FIG. 18: In vivo plasma levels of risperidone plus 9-OH-risperidone following injection of the compositions of Example 9 (different viscosities of the polymeric solution) in rabbits.
Figure 19:
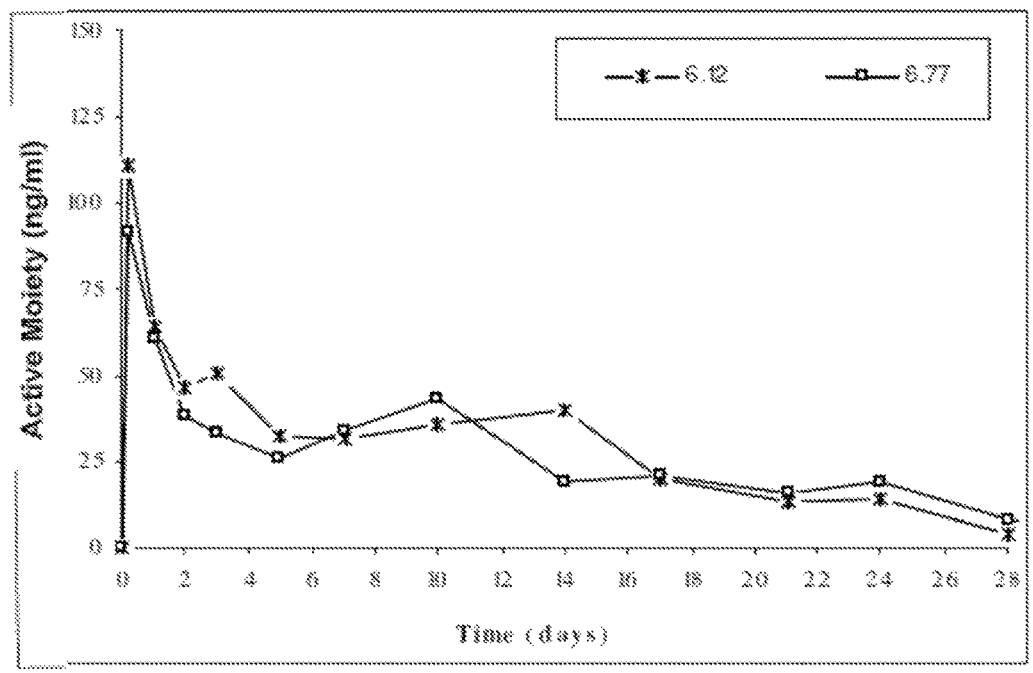
FIG. 19: In vivo plasma levels of risperidone plus 9-OH-risperidone following injection of the compositions of Example 9 (different viscosities of the polymeric solution) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIGS. 17, 18 and 19. The results are expressed as the addition of the risperidone plus 9-OH-risperidone concentrations (ng/ml) as a function of time, since the therapeutic activity of 9-OH-risperidone is substantially equivalent to that of risperidone. As depicted in the figures, the injection of an amount of formulation corresponding to 15 mg risperidone to New Zealand White rabbits with compositions having a low viscosity (0.1 Pa·s) of the polymeric solution resulted in high initial plasma levels but a fast decrease of said levels. An intermediate polymer solution viscosity (0.43 Pa·s). still provided high initial plasma levels, although their decrease was more moderate than at lower viscosity. On the contrary, higher viscosity of the polymeric solutions resulted in controlled initial plasma levels followed by significant plasma levels up at least 21 days when viscosity is over 0.5 Pa·s. In general terms, a preferred range for the viscosity of the polymer solution is between 0.5 and 7.0 Pa·s, and a more preferred range between 0.7 and 2.0 Pa·s.

EXAMPLE 10: Study of Different Drug/Polymer Mass Ratios

Risperidone implantable formulations were prepared by completely dissolving polymer Resomer® RG503 in the solvent and subsequently dispersing the drug in the appropriate amounts to obtain the following drug/polymer mass ratios, expressed as the percentage of risperidone weight in respect of the polymer+risperidone weight:

| Ingredient (mg) | | | Risperidone/Polymer mass ratio [Risperidone/(Polymer + Risperidone) |
|---|---|---|---|
| Risperidone | Polymer | Solvent | (% w/w)] |
| 15 | 85 | 140 | 15.0 |
| 15 | 60 | 140 | 20.0 |
| 15 | 45 | 83.5 | 25.0 |
| 15 | 35 | 83.5 | 30.0 |
| 15 | 30 | 70 | 33.3 |
| 15 | 27.8 | 67.8 | 35.0 |
| 15 | 25 | 100 | 37.5 |
| 25 | 33.3 | 300 | 42.9 |

The above formulations can be otherwise expressed as follows:

| Risperidone/Polymer mass ratio [Risperidone/(Polymer + Risperidone) (% w/w)] | | | | | | | |
|---|---|---|---|---|---|---|---|
| 15.0 | 20.0 | 25.0 | 30.0 | 33.3 | 35.0 | 37.5 | 40.0 |

In Vitro Release Profile:

The risperidone release from some of the formulations of this example was evaluated according to the following procedure: the amount of formulation corresponding to 25 mg of risperidone was injected from prefilled syringes equipped with a 21 G needle into flasks followed by the careful addition of a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, and periodically up to a maximum of 42 d), 5 ml of release medium was collected and replaced with fresh buffer, and the amount of risperidone present in the sample was determined by UV spectrophotometry.

Figure 20:
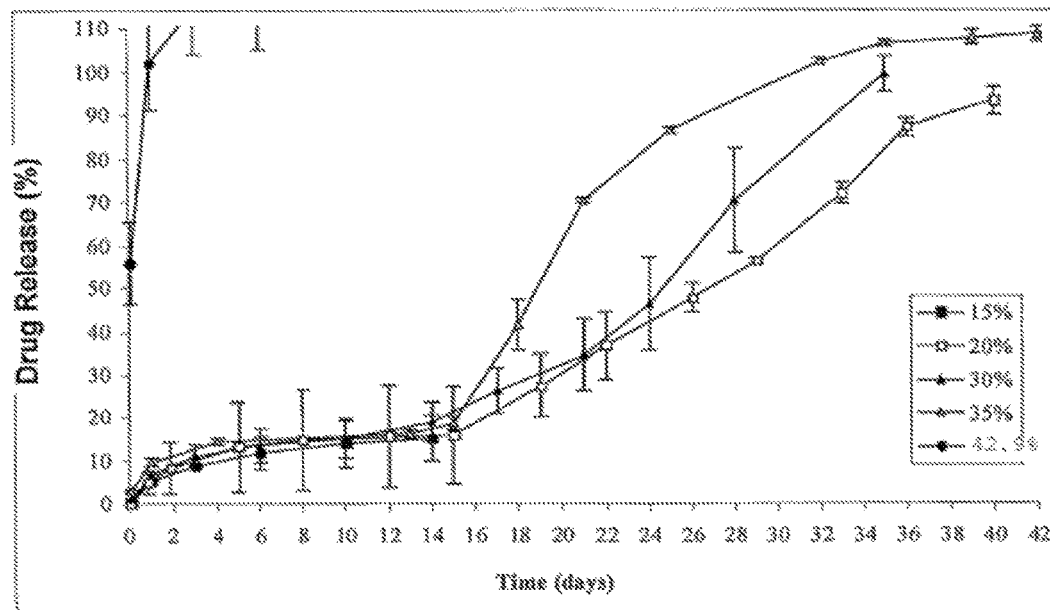
FIG. 20: In vitro release profile of risperidone for the compositions of Example 10 (different drug/polymer mass ratios in DMSO as solvent).

The profile of risperidone released from the formulations is shown in FIG. 20. The results are expressed as % Risperidone released from the formulation as a function of time. The range for the risperidone/polymer ratio between 15-35% presented in this example shows acceptable in vitro initial risperidone diffusion and a release time longer than 28 days. On the other hand, ratios of the order of 40% showed an inadequate control of the in vitro drug release, probably because the amount of polymer present in the composition was not enough for the proper risperidone entrapment into the matrix.

In Vivo Plasma Levels after Intramuscular Administration to New Zealand Rabbit

Some of the risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 21:
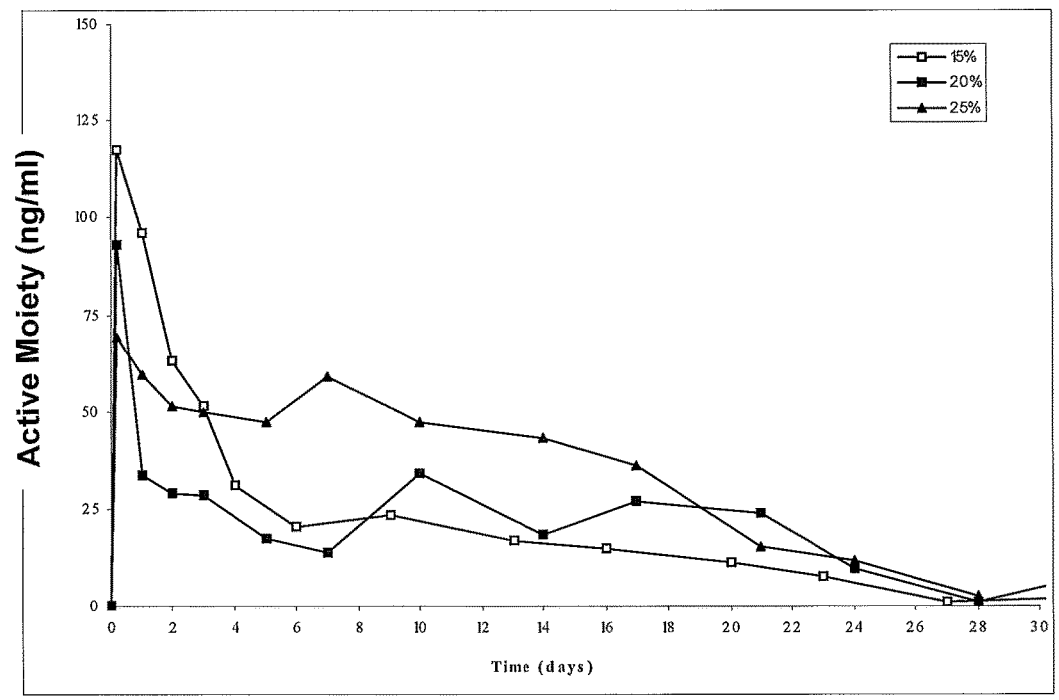
FIG. 21: In vivo plasma levels of risperidone plus 9-OH-risperidone following injection of the compositions Example 10 (different drug/polymer mass ratios) in rabbits.
Figure 22:
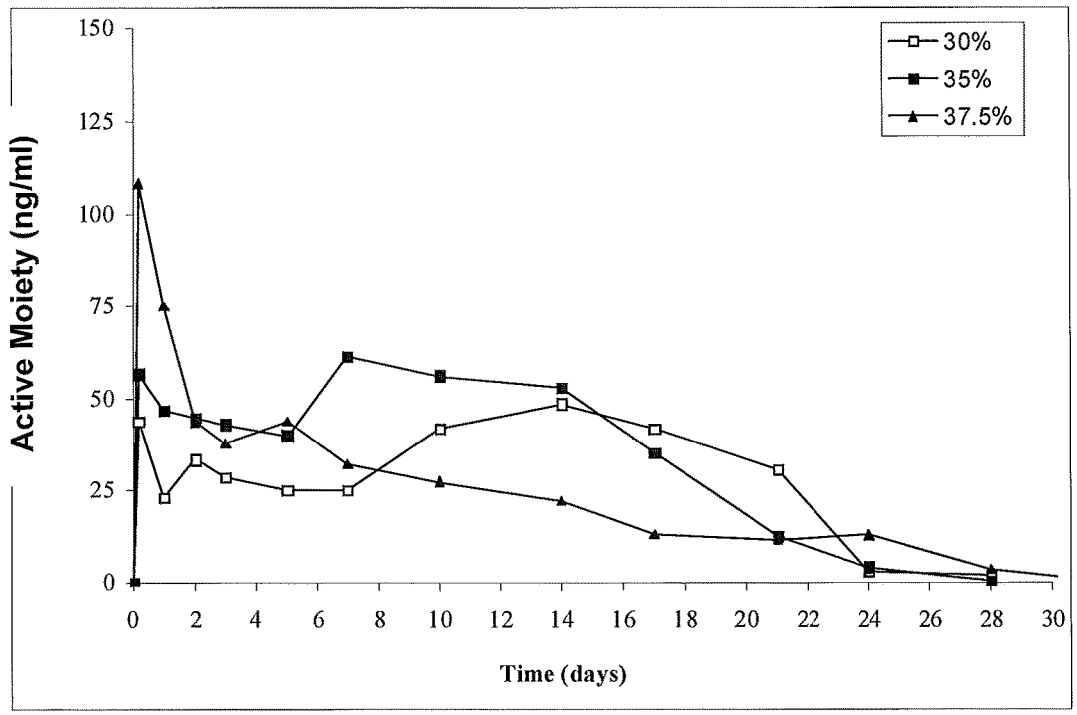
FIG. 22: In vivo plasma levels of risperidone plus 9-OH-risperidone following injection of the compositions Example 10 (different drug/polymer mass ratios) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIGS. 21 and 22. The results are expressed as the addition of the risperidone plus 9-OH-risperidone concentrations (ng/ml) as a function of time, since the therapeutic activity of 9-OH-risperidone is substantially equivalent to that of risperidone. As depicted n the figures, the injection of an amount of formulation corresponding to 15 mg risperidone to New Zealand White rabbits resulted in all the cases presented in this example to show plasma levels from the first day until at least day 24. However, in some cases, compositions resulted in moderate and well controlled initial plasma followed by sustained levels during 24 days, there being no high difference between that initial plasma levels (first day) and the ones found on the next days. Whereas in other cases, the compositions resulted in inadequately controlled initial plasma levels, showing high plasma levels during first day followed by a notably decrease during next days until plasma levels were stabilized and maintained until drug it is completely released. These finding resulted highly surprising, since it was expected that the lower drug/polymer mass ratio, the better control of the initial release due to a higher presence of polymer to entrap and retain the drug. However, what we found here, is that ratios lower than 25% could not elicit an appropriate risperidone release and showed a high diffusion from the compositions during the initial term following administration. On the other hand, ratios in the interval 25-35% were capable of providing more sustained plasma levels since the very beginning of release with lower differences between initial levels (first day) and following ones (next days). Finally, an increase in the ratio over 35% resulted in higher initial plasma levels compared to ones obtained during the next days, so that a value of 35% in this ratio is considered to represent a limit for the minimum amount of polymer which is necessary to provide a good risperidone entrapment into the composition matrix. In general terms, a preferred range for the risperidone/polymer mass ratio is between 25 and 35%. A most preferred value is around 33%.

In Vivo Plasma Levels after Intramuscular Administration to Beagle Dog

The risperidone formulations of this example corresponding to drug/polymer mass ratios of 20 and 33.3% were injected intramuscularly to Beagle dogs weighing an average of 10 kg. The amount injected corresponded to a dose of 25 mg risperidone and the composition was placed intramuscularly in the left hind leg using a syringe with a 20 G needle. Total number of dogs was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 23:
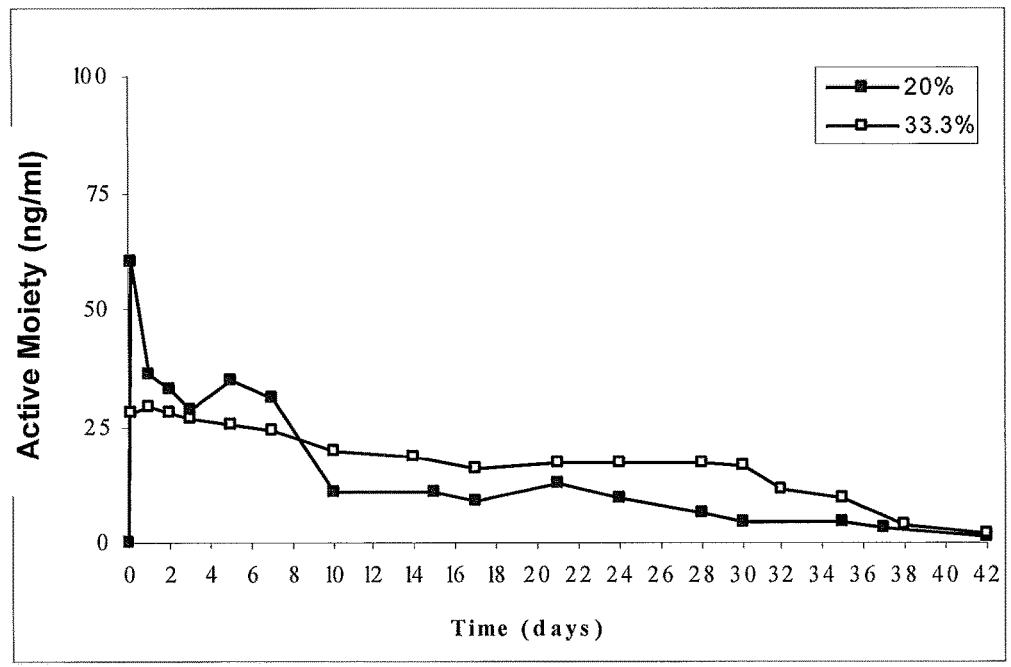
FIG. 23: In vivo plasma levels of risperidone plus 9-OH-risperidone following injection of the compositions Example 10 (different drug/polymer mass ratios) in dogs.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 23. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation corresponding to 25 mg risperidone to Beagle dogs resulted in well-controlled initial plasma levels with sustained levels up to at least 35 days. As previously described for rabbits, a higher drug/polymer mass ratio, between 25-35%, resulted in a surprisingly better control of the drug release than lower ones (below 25%), thus providing a controlled initial diffusion followed by a more constant release, so that more balanced plasma levels are obtained.

EXAMPLE 11: Study of Different Polymeric Solution/Drug Mass Ratios

The risperidone implantable formulations of this example were prepared by completely dissolving polymer Resomer®

RG503 (RG503, 50:50 lactic/glycolic acid, Boehringer Ingelheim) in dimethyl sulfoxide and subsequently dispersing the drug in the mentioned polymeric solution adjusted to different polymeric solution/risperidone mass ratios (w/w): 6.7, 10, 11.4, 14 and 19, expressed as the weight percent of polymer solution with respect to drug.

| Ingredient (mg) | | | |
|---|---|---|---|
| Risperidone | Polymer | Solvent | Polymer solution/drug mass ratio |
| 15 | 114 | 171 | 19 |
| 15 | 70.5 | 140 | 14 |
| 15 | 60 | 111.5 | 11.4 |
| 15 | 60 | 90 | 10 |
| 15 | 30 | 70 | 6.7 |

In Vivo Plasma Levels after Intramuscular Administration to New Zealand Rabbit

The risperidone composition of this example was injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 24:
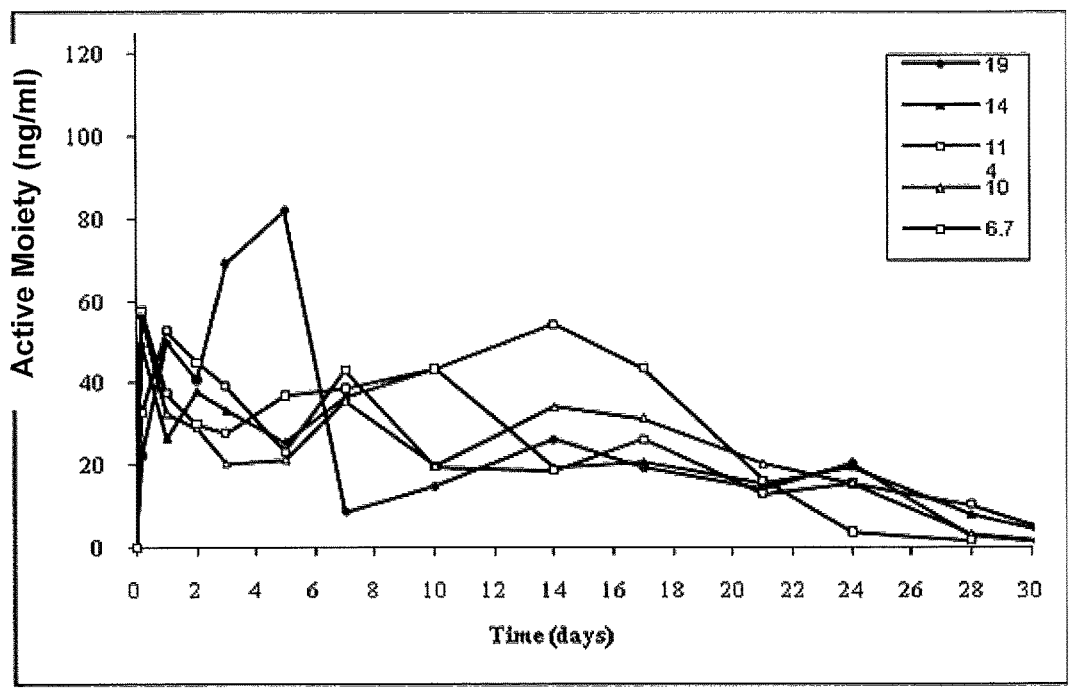
FIG. 24: In vivo plasma levels of risperidone plus 9-OH-risperidone following injection of the compositions Example 11 (different polymeric solution/drug mass ratios) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 24. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation corresponding to 15 mg risperidone to New Zealand White rabbits resulted in well-controlled initial plasma levels 4 h post-administration, which plasma levels were maintained up to 28 days in all polymeric solution/risperidone cases, although the lower the polymeric solution/risperidone ratio, the more constant levels were achieved. However the value of 19 is not considered adequate due to being capable to control the very initial release (and plasma levels) approximately during the first 24 h, but not during the following days (from day $2^{nd}$ to $5^{th}$). Therefore, an appropriate composition should comprise a polymer solution/drug mass ratio below 15 and at least until the last value tested, e.g. 4.

EXAMPLE 12: Study of Different Solvent/Drug Ratios

Risperidone implantable formulations were prepared by completely dissolving polymer Resomer® RG503 (RG503, 50:50 lactic/glycolic acid, Boehringer Ingelheim) in dimethyl sulfoxide and subsequently dispersing the drug in the mentioned polymeric solution adjusted to different solvent/risperidone ratios between 4.7 and 11.4 (w/w), expressed as weight percent of solvent with respect to drug.

| Ingredient (mg) | | | |
|---|---|---|---|
| Risperidone | Polymer | Solvent | Solvent/drug ratio |
| 15 | 114 | 171 | 11.4 |
| 15 | 70.5 | 140 | 9.3 |
| 15 | 60 | 111.5 | 7.4 |
| 15 | 60 | 90 | 6 |
| 15 | 30 | 70 | 4.7 |

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 25:
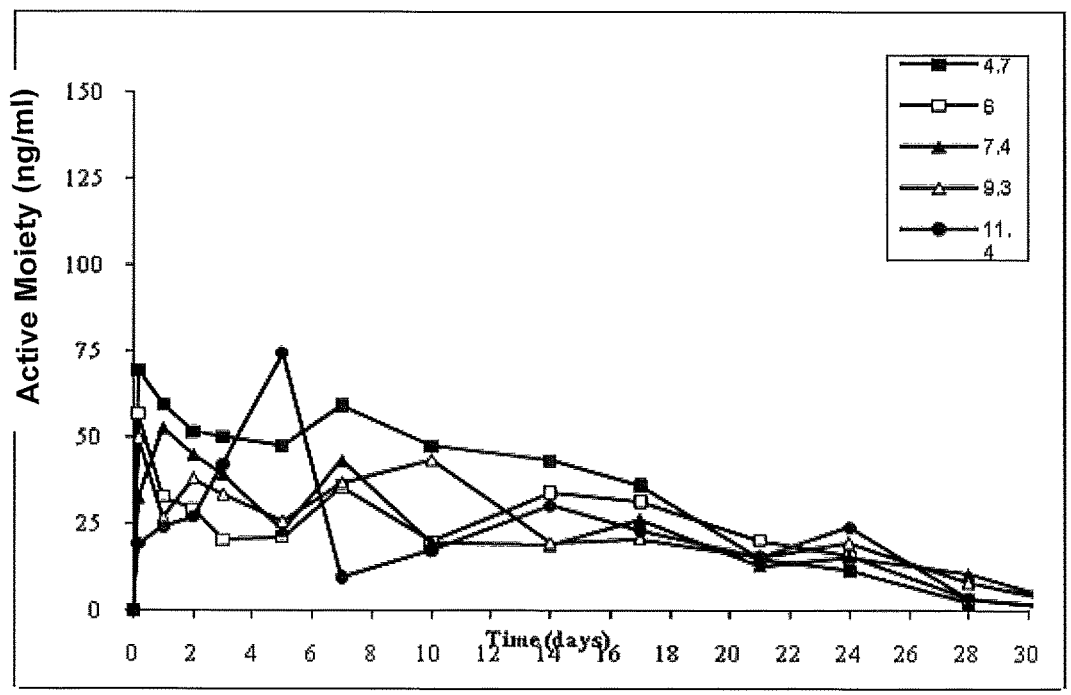
FIG. 25: In vivo plasma levels of risperidone plus 9-OH-risperidone following injection of the compositions Example 12 (different solvent/drug mass ratios) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 25. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation corresponding to 15 mg risperidone to New Zealand White rabbits resulted in initial plasma levels 4 h post-administration, which plasma levels were sustained up to 28 days in all solvent/risperidone ratios, although the lower the solvent/risperidone ratio, the more constant levels were achieved. All ratios studied provided an adequate control of the initial plasma levels during first 24 h, however, the ratio 11.4 is not considered adequate because it exhibits a later uncontrolled drug diffusion/release during the following days (days $2^{nd}$ to $5^{th}$). Therefore it is consider that an appropriate solvent/risperidone ratio should be lower than 10 and until at least the lowest value tested, e.g. 4.

EXAMPLE 13: Study of the Addition of a pH Modifier

The same risperidone implantable formulations were prepared by completely dissolving the polymer in the solvent (DMSO) and subsequently dispersing the drug in the mentioned polymeric solution with the optional addition of an alkaline agent such magnesium hydroxide.

| | Amount (mg) | |
|---|---|---|
| Ingredient | No Alkaline agent | Alkaline agent |
| Resomer®RG503 (polymer) | 100 | 100 |
| Risperidone | 25 | 25 |
| Dimethyl sulfoxide (solvent) | 233.3 | 233.3 |
| Magnesium Hydroxide | — | 8.3 |

RG503, 50:50 lactic/glycolic acid polymer (Boehringer Ingelheim)

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 26:
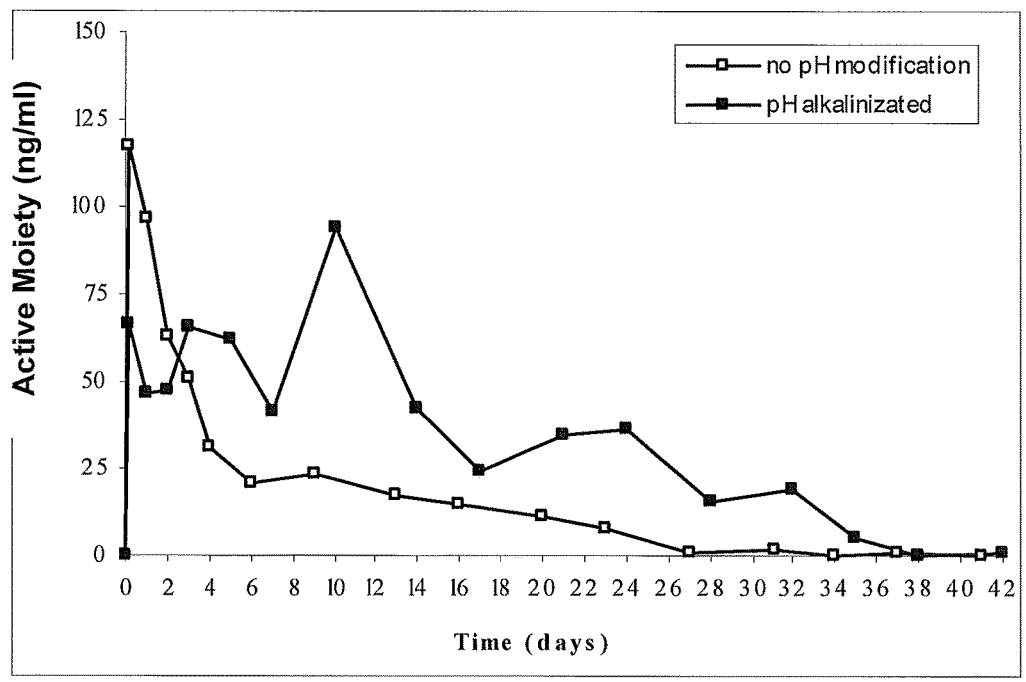
FIG. 26: In vivo plasma levels of risperidone plus 9-OH-risperidone following injection of the compositions Example 13 (optional addition of Mg(OH)$_2$) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 26. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation corresponding to 15 mg risperidone to New Zealand White rabbits resulted in initial plasma levels since 4 h post-administration up to at least 23 days. However, by including an alkaline agent within the polymer matrix, a more sustained plasma levels starting from 4 h post-administration and an increase in the time showing therapeutic risperidone plasma levels, i.e. up to at least 32 days, was achieved.

EXAMPLE 14: Study of Reconstitution of the Formulations

Risperidone implantable formulations were prepared with the following composition:

| Ingredient | Amount (mg) |
| --- | --- |
| Resomer ®RG503 (polymer) | 50 |
| Risperidone | 25 |
| Dimethyl sulfoxide (solvent) | 166.7 |

RG503, 50:50 lactic/glycolic acid polymer (Boehringer Ingelheim)

The risperidone selected for the compositions of this example showed a usual particle size distribution between 25-225 microns (not more than 10% of drug particles with a particle size smaller than 25 microns, and not more than 10% larger than 225 microns). Three different methods were applied to reconstitute the composition:

A) Vial. The polymeric solution was prepared by weighing the appropriate amounts of polymer and solvent and mixing them by vortexing until the polymer had completely dissolved in the solvent. Then, the appropriate risperidone amount was added to the polymeric solution and a homogeneous suspension was obtained by vortexing.

B) Syringes. The risperidone, the polymer and the solvent were weighed independently in syringes. The polymeric solution was then prepared by connecting the respective syringes by a fluid connector so that the solvent was moved from the syringe containing it to the syringe containing the polymer and then making several forward-backward cycles from one syringe to the other by pushing the respective plungers. Once the polymer is completely dissolved in the solvent, the third syringe containing the risperidone was connected and a homogeneous suspension was then obtained by doing several additional cycles.

C) Freeze-drying. Polymer and risperidone were freeze-dried in a prefilled syringe and the solvent was placed in a second syringe. The syringes were connected by a fluid connector and then the solvent was moved to the syringe containing the freeze-dried polymer-risperidone mixture and finally several forward-backward cycles were repeated until a homogeneous suspension was achieved.

Preparation methods B and C can also be carried out by direct connection of syringes using female-male luer syringes.

In Vitro Release Profile:

The risperidone release from formulations corresponding to the three different methods was evaluated according to the following procedure: the amount of formulation corresponding to 25 mg of risperidone was injected from prefilled syringes equipped with a 21 G needle into flasks followed by the careful addition of a pre-warmed release medium. The release medium was 250 ml phosphate buffer pH=7.4. The flasks were then placed into an oven at 37° C. and kept under horizontal shaking at 50 rpm. At previously scheduled time (2 h, 1 d, 3 d, 7 d, 10 d, 14 d, 17 d, 21 d, 24 d, 28 d, 31 d and 35 d), 5 ml of release medium was collected and replaced with fresh buffer, and the amount of risperidone amount present in the sample was determined by UV spectrophotometry.

Figure 27:
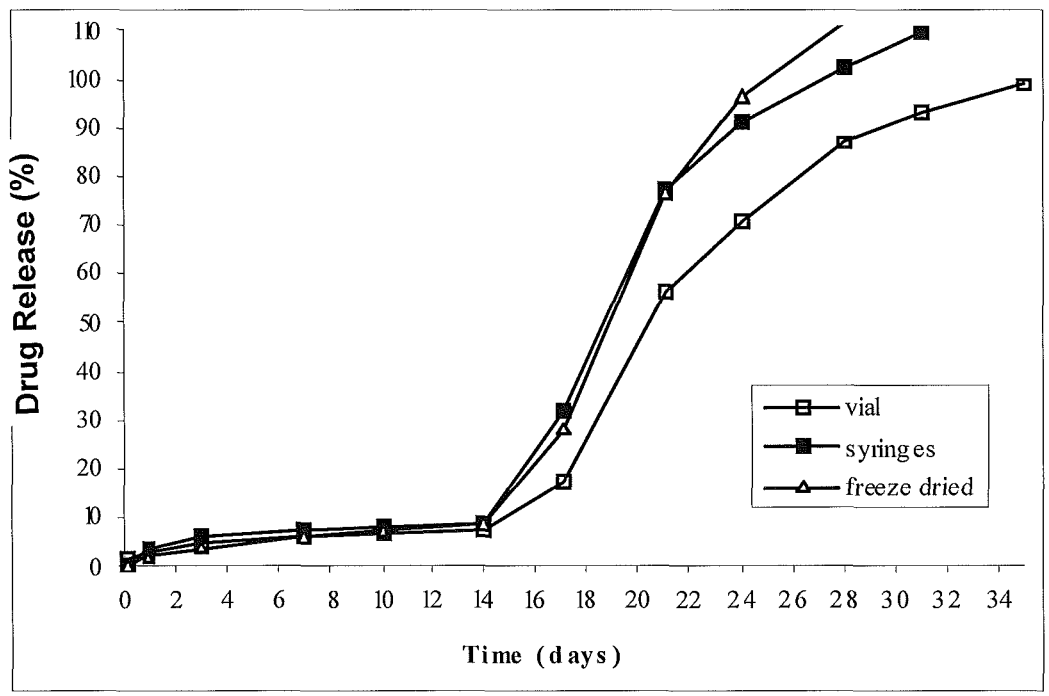
FIG. 27: In vitro release profile of risperidone for the compositions of Example 14 (different reconstitution methods).

The profile of risperidone released from the implants is shown in FIG. 27. The results are expressed as % Risperidone released from the formulation as a function of time. As depicted in FIG. 27, the release profile of the implantable formulations prepared by the three different methods was the same during first 2 weeks. However, after 14 days the preparation Method A (vial) resulted in a slightly slower release rate, probably due the higher porosity of the implants formed by the other 2 methods because of the air introduced to the formulation during the reconstitution process.

In Vivo Plasma Levels after Intramuscular Administration to New Zealand Rabbit

The risperidone compositions of this example were injected intramuscularly to New Zealand White rabbits weighing an average of 3 kg. The amount injected corresponded to a dose of 15 mg risperidone and the composition was placed intramuscularly in the left hind leg using a syringe with a 20 G needle. Total number of rabbits was 2. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 28:
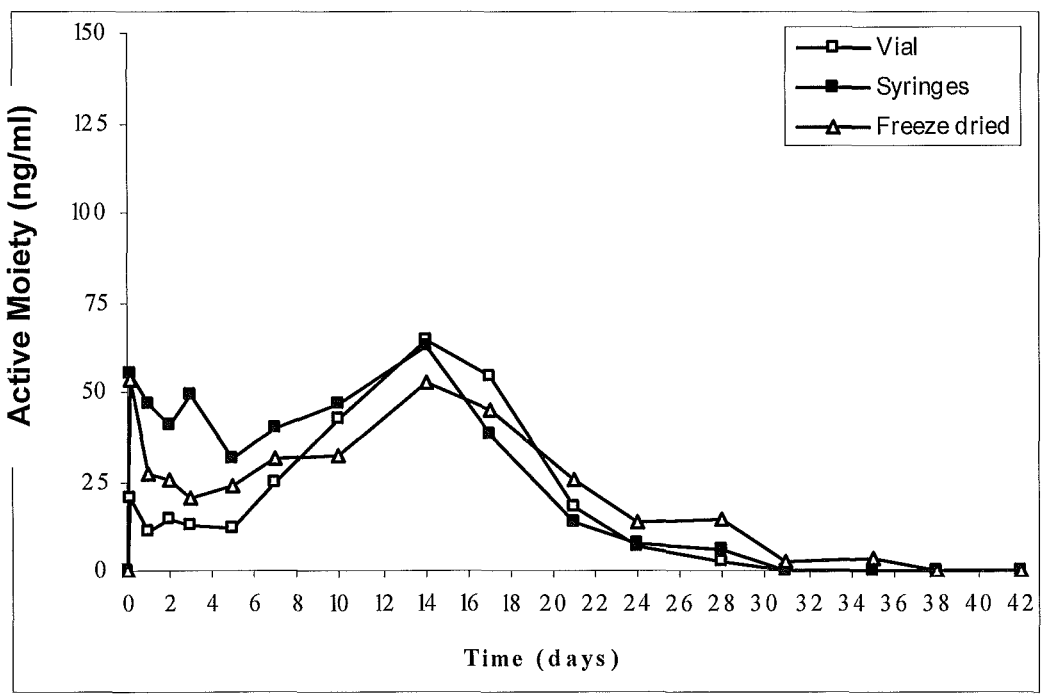
FIG. 28: In vivo plasma levels of risperidone plus 9-OH-risperidone following injection of the compositions of Example 14 (different reconstitution methods) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 28. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the injection of an amount of formulation corresponding to 15 mg risperidone to New Zealand White rabbits resulted in initial plasma levels starting from 4 h post-administration up to at least 28 days. The methods consisting on reconstitution of a formulation pre-filled in different containers by their mixing (Methods B and C) produced slightly higher initial plasma levels. This could be due to the higher porosity, and consequently higher initial diffusion, of the implantable formulations prepared by these two methods in comparison with Method A (preparation inside a vial). This fact could be also the reason for their higher plasma levels during the first week after administration.

In Vivo Plasma Levels after Intramuscular Administration to Beagle Dog

The risperidone formulations of this example were also injected intramuscularly to Beagle dogs weighing an average of 10 kg. The amount injected corresponded to a dose of 25 mg risperidone and the composition was placed intramuscularly in the left hind leg using a syringe with a 20 G needle. Total number of dogs was 3. After injection, plasma levels were obtained at 0, 4 h, 1 d, 2 d, 3 d, 5 d, 7 d, 10 d, 14 d, 17 d, 21 d, 24 d, 28 d, 31 d, 35 d, 38 d and 42 d.

Figure 29:
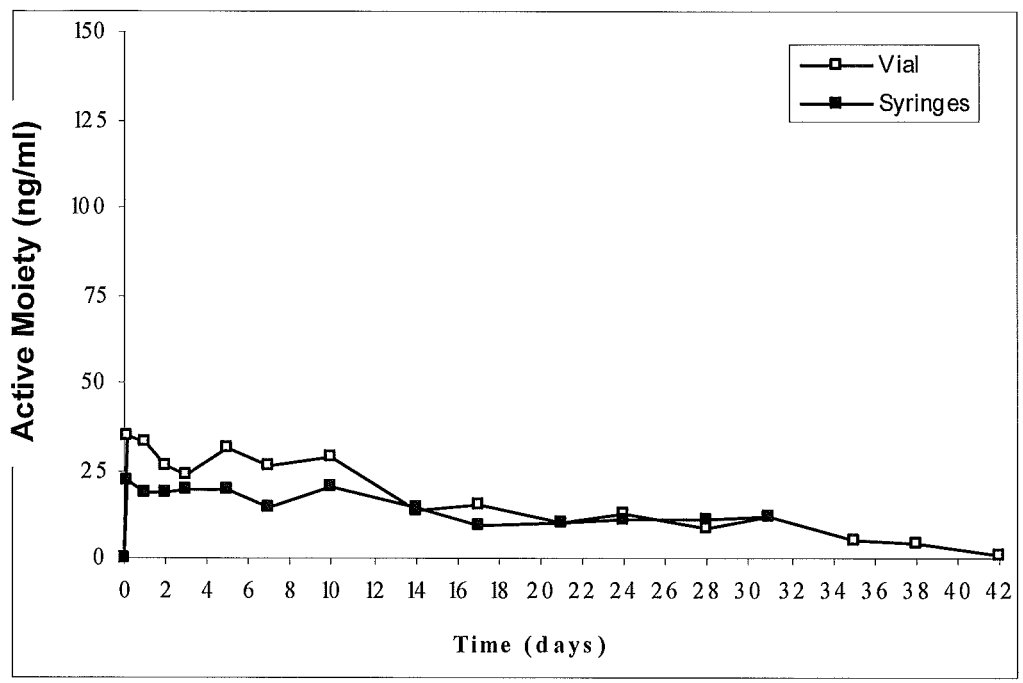
FIG. 29: In vivo plasma levels of risperidone plus 9-OH-risperidone following injection of the compositions of Example 14 (different reconstitution methods) in dogs.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 29. The results are expressed as the addition of the risperidone plus 9-OH-risperidone concentrations (ng/ml) as a function of time, since the therapeutic activity of 9-OH-risperidone is substantially equivalent to that of risperidone. As it can be seen in the cited figure, the injection of an amount of formulation corresponding to 25 mg risperidone to Beagle dogs resulted in well-controlled initial plasma levels with sustained levels up to at least 35 days using different preparation methods such as prior elaboration of polymeric solution followed by drug addition (vial, method A) or by direct reconstitution starting from solid components (syringes, method B).

EXAMPLE 15: Study of the Effect of Sterilization by Irradiation Process

In the present example, the composition of the risperidone implantable formulations was as follows maintaining always the same amounts of drug, polymer and solvent: Risperidone 15 mg, Polymer 30 mg and Solvent 70 mg.

| Composition | Irradiation (KGy) | Polymer lactic/glycolic ratio | Polymer End Terminal group | Mean Molecular weight (g/mol) | Polymer Solution Viscosity (Pa·s) | Solvent |
|---|---|---|---|---|---|---|
| A | 0 | 50:50 | capped | 27,020 | 1.62 | DMSO |
| B | 10 | 50:50 | capped | 23,189 | 1.30 | DMSO |
| C | 15 | 50:50 | capped | 22,182 | 1.00 | DMSO |
| D | 25 | 50:50 | capped | 20,991 | 0.81 | DMSO |
| E | 0 | 50:50 | capped | 39,708 | 5.97 | DMSO |
| F | 25 | 50:50 | capped | 27,891 | 1.78 | DMSO |

The implantable formulations were prepared by direct reconstitution of 2 prefilled syringes, first one with polymer and risperidone mixture, and second one with the solvent. Syringes were connected.

Syringes containing polymer plus risperidone mixtures were sterilized by β-irradiation in the range 10-25 KGy. As indicated in the table, two different polymers were tested, one is an end capped 50:50 polymer with mean Mw 27,020 g/mol, non irradiated or irradiated at 10, 15 or 25 KGy, and the other an end capped 50:50 polymer with mean Mw 39,708 g/mol, non irradiated or irradiated at 25 KGy.

Formulations A and E received sterilization irradiations that gave rise to different compositions due to different polymer molecular weight losses during the process; however, the inherent viscosity did not fall below 0.25 dL/g in any case, and the viscosity of the polymer solution remained in the range of about 0.5-7 Pa·s, which range previously established as being adequate for forming long lasting implantable formulations (Example 9), i.e. formulations exhibiting a release profile last at least 14 days.

Figure 30:
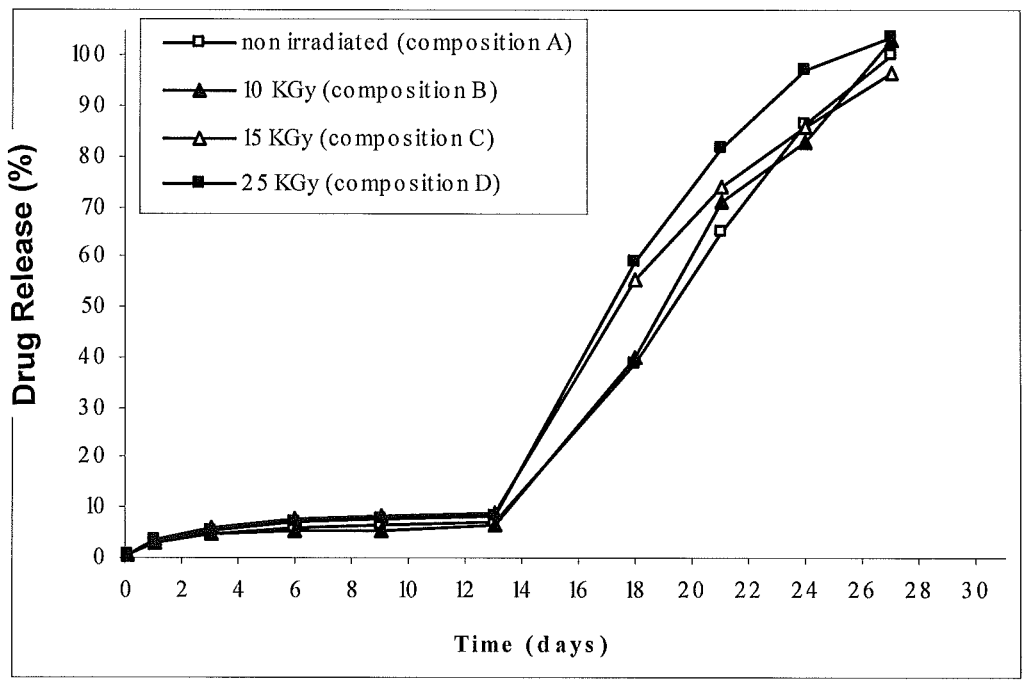
FIG. 30: In vitro release profile of risperidone for the compositions of Example 15 (sterilization by irradiation).
Figure 31:
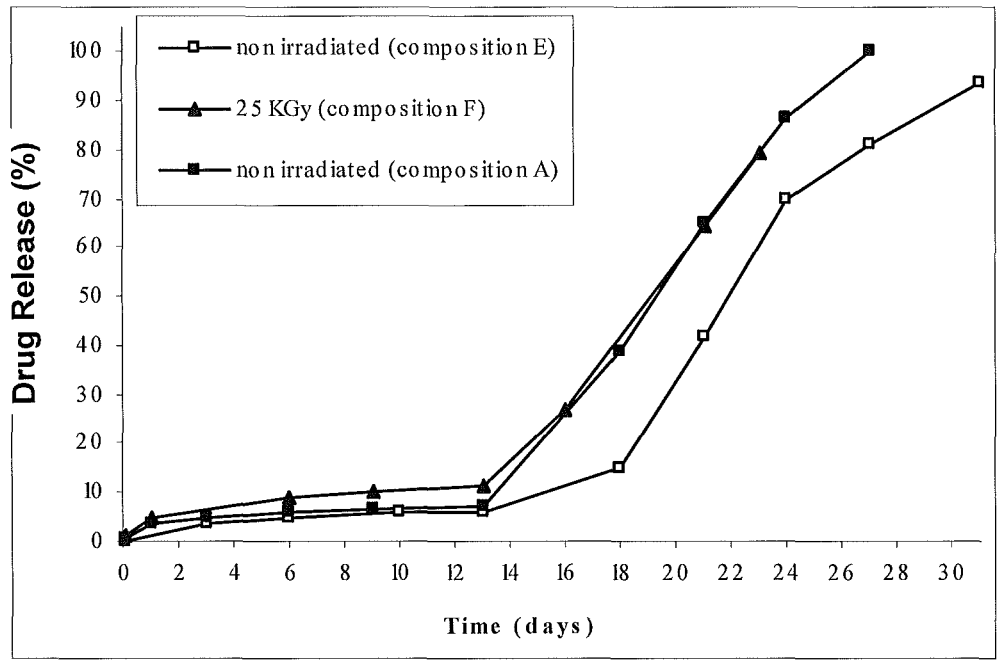
FIG. 31: In vitro release profile of risperidone for the compositions of Example 15 (sterilization by irradiation).

In Vitro Release Profile:

The risperidone release from compositions of this example was evaluated according to the following procedure. The amount of formulation corresponding to 25 mg of risperidone was injected from prefilled syringes equipped with a 21 G needle into flasks having a pre-warmed release medium. The release medium was 250 ml phosphate buffer, pH=7.4. The flasks were then placed into an oven at 37° C. and kept under horizontal shaking at 50 rpm. At previously scheduled time points (2 h, 1 d, and periodically up to 28 days) 5 ml of release medium was collected and replaced with fresh buffer and the amount of risperidone present in the sample was determined by UV spectrophotometry. The profile of risperidone released from the implants of this example is shown in FIG. 30 and FIG. 31. The results are expressed as % drug released from implants as a function of time.

As depicted in FIG. 30, the release of risperidone from the same formulation either non irradiated (composition A) or irradiated at different levels (compositions B, C and D) in the range 10-25 KGy resulted in very similar profiles because polymer solution viscosities were still within the preferred established range 0.7 to 2.0 Pa·s. FIG. 31 shows how the other polymer with a higher Mw (39,708 g/mol) (composition E) which presents an slightly slower release profile, once it is irradiated (composition F) presents a release profile closer to the non-irradiated lower Mw polymer (composition A), due to the loss of molecular weight during sterilization process, which leads to a composition with polymer solution viscosity key parameter within preferred ranges 0.7-2.0 Pa·s.

In Vivo Plasma Levels after Intramuscular Administration to New Zealand Rabbit:

The risperidone compositions A, B, C, D and G of this example were injected intramuscularly to New Zealand White rabbits weighing an average of 3 kg. The amount injected corresponded to a dose of 15 mg risperidone, and the composition was placed intramuscularly in the left hind leg using a syringe with a 20 G needle. Total number of rabbits per composition was 3. After injection, plasma levels were obtained at 0, 4 h, 1 d, 2 d, 5 d, 7 d, 10 d and periodically up to 28 days.

Figure 32:
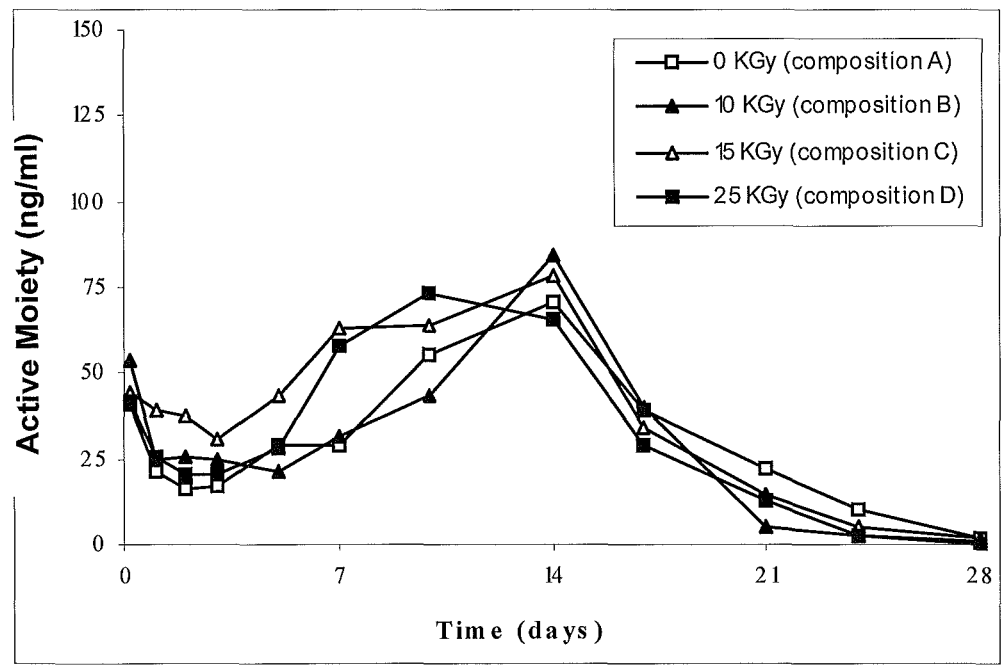
FIG. 32: In vivo plasma levels of risperidone plus 9-OH-risperidone following injection of the compositions of Example 15 (sterilization by irradiation) in rabbits.
Figure 33:
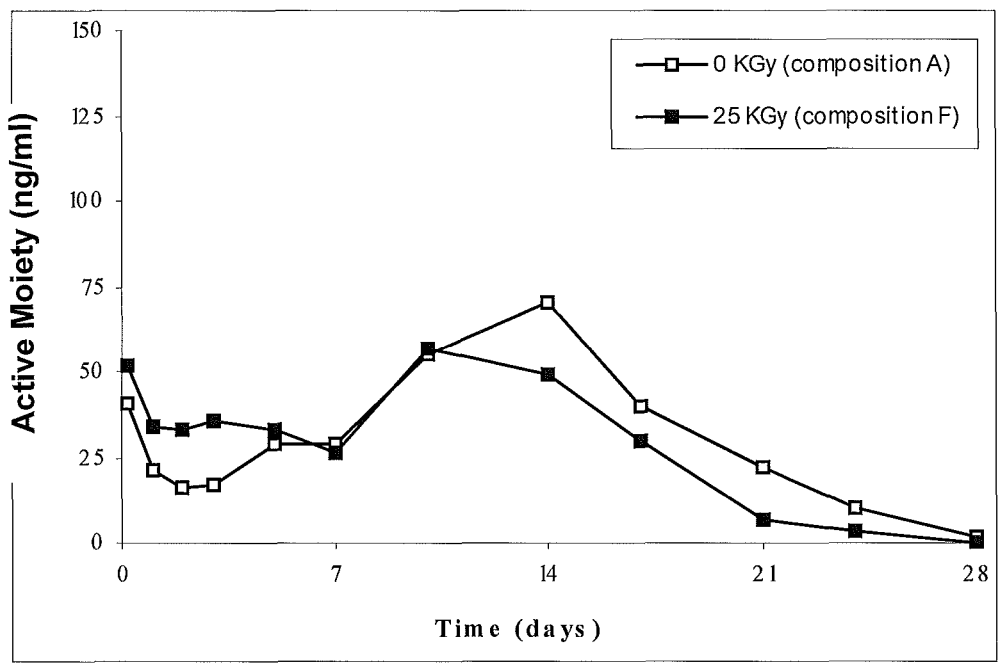
FIG. 33: In vivo plasma levels of risperidone plus 9-OH-risperidone following injection of the compositions of Example 15 (sterilization by irradiation) in rabbits.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 32 and FIG. 33. The results are expressed as the addition of the risperidone plus 9-OH-risperidone concentrations (ng/ml) as a function of time, since the therapeutic activity of 9-OH-risperidone is substantially equivalent to that of risperidone. As demonstrated in these figures, the injection of an amount of composition equivalent to 15 mg risperidone to New Zealand White rabbits resulted in very similar plasma levels as could be predicted since in vitro behaviour was very similar after irradiation. FIG. 32 revealed not extraordinary changes in the risperidone active moiety plasma levels when a formulation comprising a 27,020 g/mol mean molecular weight polymer (composition A), was irradiated at 10, 15 or 25 KGy (composition B, C and D, respectively) since key parameter such as polymer solution viscosity is still inside the previously preferable determined range of 0.7 to 2.0 Pa·s.

A higher molecular weight polymer (39,708 g/mol), with polymer solution viscosity out of the preferable range (5.97 Pa·s, composition E), upon irradiation at 25 KGy (since higher molecular weight polymers suffer proportionally higher molecular weight losses during irradiation) leads to a polymer with lower inherent viscosity and consequently lower but still adequate polymer solution viscosity of 1.78 Pa·s (composition F). That higher molecular weight polymer, after 25 KGy irradiation, resulted extremely close to the lower one without any irradiation (composition A) in both molecular weight and polymer solution viscosity, therefore fulfilling in this manner the polymer solution viscosity parameter leading to adequate long lasting implantable systems in line with the present invention, and experimenting a very similar in vivo behaviour (plasma levels profile) as shows FIG. 33.

COMPARATIVE EXAMPLE 2: Not According to the Invention

Risperidone implantable formulations (Prodex 2 and Prodex 4C) were prepared according to procedures described in U.S. Pat. No. 5,688,801.
In Vivo Plasma Levels after Intramuscular Administration to Beagle Dog
The risperidone formulations of this example were injected intramuscularly to Beagle dogs weighing an average of 10 kg after resuspension of microparticles in 2 ml of a 2.5% (in weight) carboxymethyl cellulose solution in water. The amount injected corresponded to a dose of 25 mg risperidone and the composition was placed intramuscularly in the left hind leg. Total number of dogs was 6. After injection, plasma levels were obtained at 0, 1 d, 2 d, 6 d, 9 d, 13 d, 15 d, 17 d, 19 d, 21 d, 23 d, 26 d, 29 d, 33 d, 35 d, 42 d and 56 d.

Figure 34:
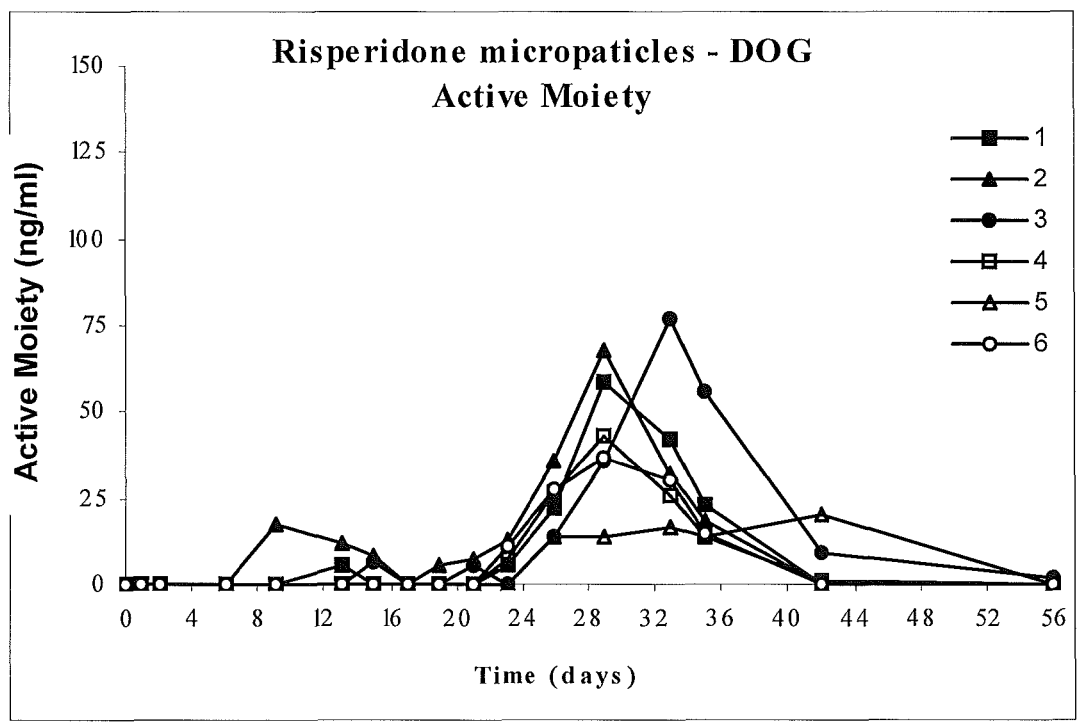
FIG. 34: In vivo plasma levels of risperidone plus 9-OH-risperidone following injection of the compositions of Comparative Example 2 (compositions obtained through the procedures of the prior art) in dogs.

The kinetics of the plasma levels corresponding to the risperidone active moiety was evaluated by measuring both risperidone and its active metabolite 9-OH-risperidone in the plasma samples. The profile of the risperidone active moiety plasma levels is shown in FIG. 34. The results are expressed as the addition of the risperidone plus 9-OH-risperidone concentrations (ng/ml) as a function of time, since the therapeutic activity of 9-OH-risperidone is substantially equivalent to that of risperidone. As depicted in the figure, the results of this test showed that the administration of risperidone in preformed microparticles, according to procedures described in the prior art, fails to provide significant plasma levels of risperidone active moiety in dogs until the third week following administration. The plasma levels observed among the 6 animals also showed a poor reproducibility, and the rise was typically observed from approximately day $21^{st}$ until approximately day $28^{th}$ following administration, to then diminish at a similar rate, thereby providing a peak of plasma level with an approximate extension of 2 weeks. These profiles are completely different to the profiles observed in the examples according to the invention and clearly demonstrates the difference between the plasma levels obtained with the composition according to the invention compared to those obtained according to the prior art.

From the above experiments it can be concluded that the viscosity of the polymeric solution (polymer+solvent), surprisingly shows a stronger influence on the control of the drug release than other various factors that could conceivably be considered as having a stronger effect, such as the nature of the polymer or its concentration. This result is unexpected and surprising in the light of the prior art.

It can also be concluded that, when a certain portion of the polymer is removed at a constant risperidone amount,—or, in other words, that the drug/polymer mass ratio is increased—, the initial release is lower and consequently the plasma level profiles are flattened. This effect is likewise surprising, since the presence of a lower amount of polymer could be a priori related to a lower capacity to retain the drug and providing a worse initial release control.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

The invention claimed is:
1. An injectable depot composition consisting of:
drug, which is risperidone present as particles having a particle size distribution as follows: not more than 10% of the total volume of drug particles is less than 10 microns in size, not more than 10% of the total volume of drug particles is greater than 225 microns in size, and the d0.5 of the size distribution is in the range of about 60-130 microns; and
polymeric solution consisting of:
DMSO; and
biocompatible poly(lactide-co-glycolide) (PLGA) copolymer comprising lactic acid and glycolic acid monomers, wherein the monomers are present at a monomer ratio of lactic to glycolic acid of 48:52 to 52:48, the copolymer has an inherent viscosity in the range of 0.25-0.48 dl/g as measured in chloroform at 25° C. and at a concentration of 0.1% wt/v with a Ubbelohde size 0c glass capillary viscometer; wherein
the polymeric solution has a viscosity in the range of about 0.7 Pa.s to about 3.0 Pa.s; and wherein
the drug content is about 13% wt with respect to the total composition weight;
the DMSO to drug mass ratio is about 4:1 to 5:1;
the polymeric solution to drug mass ratio is about 6.5:1 to 7:1.
2. The injectable depot composition according to claim 1, wherein the drug/copolymer mass ratio is about 33%, expressed as the weight percentage of the drug with respect to the drug plus copolymer.
3. The injectable depot composition according to claim 1, wherein the DMSO to drug mass ratio is about 4.66:1.
4. The injectable depot composition according to claim 1, wherein the mass ratio between the weight of the polymeric solution and the weight of the drug is about 6.66:1.
5. The injectable depot composition according to claim 1, wherein the composition is a sterile composition.
6. A pharmaceutical kit suitable for the in situ formation, in a subject, of a biodegradable implant comprising the injectable depot composition according to claim 1, wherein, prior to mixing with the DMSO the drug and the biocompatible copolymer are contained in a first container, and the DMSO is contained in a second, separate container.
7. The pharmaceutical kit according to claim 6, wherein at least one of the first and second containers is a syringe, a vial, or a cartridge.
8. The pharmaceutical kit according to claim 7, wherein both the first and the second containers are disposable syringes.

9. The pharmaceutical kit according to claim 8, wherein the syringes are connectable through a connector device or a direct thread.

10. The injectable depot composition according to claim 1, wherein at least 95% wt of the copolymer is dissolved in the composition prior to placement in an aqueous environment.

11. The injectable depot composition according to claim 1, wherein ≥1% wt of the drug is dissolved in the DMSO or the composition prior to placement in an aqueous environment.

12. The injectable depot composition according to claim 1, wherein the composition is injectable by hand through a 18 to 22 gauge needle.

13. The injectable depot composition according to claim 1, wherein, prior to inclusion in the injectable composition, the copolymer has been irradiated with about 10 KGy to about 25 KGy of beta-radiation.

14. The injectable depot composition of claim 1, wherein the composition releases at least 0.5% wt and no more than 8% wt of its charge of risperidone within 24 hours after being placed in an aqueous environment.

15. The injectable depot composition of claim 1, wherein the composition provides a substantially level plasma concentration profile of within ±15% of the average or mean plasma concentration during a period of at least 14 days following administration of the composition to a subject.

16. The injectable depot composition of claim 15, wherein the composition provides a plasma profile defined as follows:

| Dose (mg) | Cmin (ng/ml) | Cavg (ng/ml) | Cmax (ng/ml) |
|---|---|---|---|
| 25-150 | 1-80 | 3-200 | 8-300 | during a dosing period of at least 14 days following administration to a subject of an amount of the injectable composition equivalent to the dose indicated.

17. The injectable depot composition of claim 1, wherein: a) the mass ratio of the amount of polymeric solution to the amount of drug in the injectable composition is about 6.66:1; and b) the DMSO to drug mass ratio is about 4.66:1.

18. The injectable depot composition of claim 1, wherein the composition provides a substantially level plasma concentration profile of within ±10% of the average or mean plasma concentration during a period of at least 14 days following administration of the composition to a subject.

19. The injectable depot composition of claim 18, wherein the composition provides a plasma profile defined as follows:

| Dose (mg) | Cmin (ng/ml) | Cavg (ng/ml) | Cmax (ng/ml) |
|---|---|---|---|
| 25-150 | 1-80 | 3-200 | 8-300 | during a dosing period of at least 28 days following administration to a subject of an amount of the injectable composition equivalent to the dose indicated.

20. The injectable depot composition of claim 1, wherein the composition provides a substantially level plasma concentration profile of within ±20% of the average or mean plasma concentration during a dosing period of at least 28 days following administration of the composition to a subject.

* * * * *